United States Patent [19]

Phillipps et al.

[11] 3,943,124

[45] Mar. 9, 1976

[54] CHEMICAL COMPOUNDS

[76] Inventors: Gordon Hanley Phillipps, 8 Sudbury Hill Close, Wembley, Middlesex; Christopher Earle Newall, 138 Princes Ave., Acton, London W. 3, both of England

[22] Filed: June 20, 1974

[21] Appl. No.: 481,227

Related U.S. Application Data

[63] Continuation-in-part of Ser. Nos. 208,923, Dec. 16, 1971, and Ser. No. 369,277, June 12, 1973.

[30] Foreign Application Priority Data

June 15, 1972 United Kingdom............... 28118/72
Dec. 17, 1970 United Kingdom............... 60070/70

[52] U.S. Cl... 260/239.55 R; 260/397.1; 260/397.4; 260/397.45; 260/397.5; 424/241
[51] Int. Cl.$^2$............................................ C07J 17/00
[58] Field of Search..... 260/397.1, 239.55 R, 397.4, 260/397.5, 397.45

[56] References Cited
UNITED STATES PATENTS

| | | | |
|---|---|---|---|
| 3,828,080 | 8/1974 | Phillipps et al. | 260/397.1 |
| 3,856,828 | 12/1974 | Phillipps et al. | 260/397.1 |

*Primary Examiner*—Elbert L. Roberts
*Attorney, Agent, or Firm*—Bacon & Thomas

[57] ABSTRACT

Steroids of the androstane series having a 3α-hydroxy group, a 3β-hydrogen or methyl group; a 10-hydrogen atom or methyl group, an 11-oxo group or two hydrogen atoms at the 11-position, a 17α-hydrogen atom, and a group at the 17β-position which is esterified carboxyl group, an N-mono or di-substituted carbamoyl group, a cyano group, a formyl group or an acetalised formyl group; and the 3α-esters thereof.

The steroids possess anaesthetic properties.

28 Claims, No Drawings

CHEMICAL COMPOUNDS

The present Application is a continuation-in-part of Application No. 208,923 filed 16 Dec. 1971 and Application No. 369,277 filed 12th June 1973 both of Gordon Hanley Phillipps and Christopher Earle Newall.

This invention is concerned with improvements in or relating to compounds of the androstane series having useful anaesthetic activity.

It has long been known that a number of steroids give rise to profound depression of the central nervous system and act pharmacodynamically as anaesthetics or hypnotics. Such compounds have been the subject of considerable study in an attempt to find anaesthetics to replace such substances as thiopentone sodium normally used but well known to be accompanied by some degree of hazard and disadvantage. The literature shows that very many steroid compounds have been studied in this regard. Reviews and discussions of some of the work carried out are to be found, for example, in "Methods in Hormone Research" (Edited by Ralph I. Dorfman, Vol. III, Part A, Academic Press, London and New York, 1964, pages 415–475); H. Wilzel, Z. Vitamin Hormon-Fermentforsch 1959, 10, 46–74; H. Selye, Endocrinology, 1942, 30, 437–453; S. K, Figdor et al., J. Pharmacol. Exptl. Therap., 1957, 119, 299–309 and Atkinson et al., J. Med. Chem. 1965, 8, 426–432.

A thorough review of the literature indicates that anaesthetic steroids generally possess poor activity and/or long induction periods. With such compounds a variety of undesired side effects such as paraesthesia and vein damage have been noted. Steroids possessing anaesthetic activity hitherto described are generally relatively simple pregnane derivatives, often hydroxylated in the 3-position, the general trend having been in the latter case to study 3β-hydroxy compounds rather than 3α-hydroxy compounds.

We have now found that certain compounds of the androstane series which possess inter alia a 3α-hydroxy group and which are more particularly described hereinafter have remarkable anaesthetic properties.

The new androstane compounds with which the invention is concerned may be generally characterised as being steroids of the androstane series having anaesthetic properties and further characterised by possessing a hydroxy group in the α-configuration at the 3-position, a hydrogen atom or a methyl group in the 3β-position, a keto group or two hydrogen atoms at the 11-position, a hydrogen atom at the 17-position in the α-configuration, and a group R at the 17-position in the β-configuration which is an esterified carboxyl group, an N-mono or di-substituted carbamoyl group, a cyano group, a formyl group or an acetalised formyl group.

U.S. Pat. Application No. 208959 of Cook et al filed Dec. 16 1971 describes and exemplifies a 3α-hydroxy 5α-androstane having a 17β-methoxycarbonyl group, two hydrogen atoms at the 11-position and a double bond at the 1,2-position.

Compounds in the androstane series having a 17β-methoxycarbonyl group and 3α-hydroxy group are known in the 5β-series (where either two hydrogen atoms or an oxo group are present at the 11-position) and in the 5α-series (where two hydrogen atoms are present at the 11-position), the steroid nucleus being otherwise saturated and unsubstituted. No anaesthetic or other physiological activity has previously been ascribed to these three compounds.

The expression "androstane series" as used herein includes not only compounds of the conventional androstane ring structure but also the corresponding 19-nor compounds. Unsaturated androstanes, for example $\Delta^{8(9)}$ and/or $\Delta^1$ or $\Delta^4$ steroids, are also included. The steroids of the invention include 5α-compounds, 5β-compounds and compounds in which a double bond is present at the 5-position.

In general, the 3α-hydroxy-androstane anaesthetics of this invention have been found to induce anaesthesia with generally short induction periods, the anaesthetic action at suitable doses being in general instantaneous; the compounds are thus excellent anaesthetics for inducing anaesthesia which is to be maintained e.g. by an inhalation anaesthetic such as ether, halothane, nitrous oxide, trichloroethylene etc. The compounds are however capable of maintaining anaesthetia and analgesia to a sufficient degree to enable various surgical operations to be conducted without the aid of an inhalation anaesthetic, the required degree of anaesthesia being maintained if necessary by repeated administration (or even continuous administration). Moreover, the said anaesthetics in accordance with the invention in general give rise to minimal sideeffects compared to previously described steroidal anaesthetics.

The invention further includes 3α-esters of the 3α-hydroxy-androstane anaesthetics of this invention, particularly lower alkanoyl esters, for example containing in the alkanoyl group up to 5 carbon atoms. Such esters may also be esters containing one or more substituents in the alkanoyl portion e.g. carboxyl groups, amino or substituted amino groups or halogen atoms etc. Generally the induction period of a 3-ester is longer than that of a corresponding 3α-hydroxy compound. Both the 3α-hydroxy compounds and the corresponding 3-esters may be regarded as central nervous system depressants and thus in suitable dose may also be used as hypnotics or sedatives.

The above defined 3α-hydroxy androstane anaesthetic steroids and the corresponding 3α-esters are hereinafter referred to as 3α-oxygenated androstane anaesthetics.

In general, we particularly prefer steroids according to the invention having an 11-keto group and a 5α-hydrogen atom or a 4,5-double bond.

Steroids according to the invention in which the 17-substituent is a cyano group are particularly advantageous.

The 17-substituent R may usefully be a group of the formula -$COR^1$ where $R^1$ is (I) a substituted or unsubstituted aryloxy group; (II) a substituted or unsubstituted aralkoxy group; (III) a group of the formula -$NR^4R^5$ wherein $R^4$ and $R^5$ are the same or different; $R^4$ is (i) an alkyl group, (ii) an aralkyl group which may be substituted or unsubstituted, or (iii) an aryl group which may be unsubstituted or substituted; $R^5$ is a hydrogen atom or an $R^4$ group; or wherein $R^4$ and $R^5$ taken together with the nitrogen atom represent a heterocyclic ring which may contain a further hetero-atom and may be unsubstituted or substituted; (IV) a straight or branched chain alkoxy group which may be unsubstituted or substituted; (v) an O-cycloaliphatic group; or (vi) an O-heterocyclic group bonded to said O-atom by a C-O-bond.

In general, those of the above groupings which comprise alkyl portions preferably contain 1–10, more preferably 1–6, carbon atoms in these portions (e.g. a methyl or ethyl group). Aryl and aralkyl groups are preferably monocyclic (e.g. phenyl and benzyl) and may carry substituents such as alkyl groups, hydroxyl or lower alkoxy groups, alkythio groups, alkoxy carboxyl groups, nitro groups or halogen atoms. N-attached and C-attached heterocyclic groups may be saturated or unsaturated, substituted or unsubstituted, monocyclic or bicyclic and may contain one or more heteroatoms such as nitrogen, oxygen or sulphur. They preferably have 5–10, e.g. 5 or 6, ring members and include, for example, piperidino, piperazino and morpholino groups which may carry one or more alkyl, e.g. methyl, substituents. Halogen substituents may, for example, be chlorine atoms. Acyloxy groups are preferably lower alkanoyloxy groups such as acetoxy groups. Cycloaliphatic groups may be cycloalkyl groups such as cyclohexyl which may carry substituents such as a morpholino group.

Thus, for example $R^1$ may be an aryloxy group substituted by one or more hydroxy or alkoxy groups containing 1–10, preferably 1–6 carbon atoms; or a straight or branched chain alkoxy group substituted by one or more halogen (e.g. chlorine) atoms or aryl (e.g. phenyl), hydroxy, acyloxy (e.g. acetoxy), cyano, alkoxy-carbonyl (e.g. ethoxy carbonyl), alkoxy (which may itself be substituted by an $-NR^4R^5$ or $NH_2$ group) or $-NR^4R^5$ or $-NH_2$ groups $R^4$ and $R^5$ may for example be methyl or ethyl groups or aryl groups which may be substituted by one or more alkoxy groups having 1–6 carbon atoms or halogen atoms. $R^4$ and $R^5$ together with the nitrogen atom may be a heterocyclic ring which may contain a further hetero atom e.g. a nitrogen, sulphur or oxygen atom and/or may carry one or more alkyl substituents having 1–6 carbon atoms or aryl (e.g. phenyl) groups.

R may especially usefully be a group of the formula -$COR^1$ where $R^1$ is (i) an alkoxy group having 1–6 carbon atoms which may be unsubstituted or substituted by a hydroxy, acyloxy or N-morpholino group; or (ii) a group of the formula -$NR^2R^3$ wherein $R^2$ represents an alkyl group having 1–4 carbon atoms and $R^3$ represents an alkyl group having 1–4 carbon atoms or a hydrogen atom, or wherein $R^2$ and $R^3$ taken together with the nitrogen atom represent a heterocyclic ring which may contain a further nitrogen or oxygen atom.

Representative groups $R^1$ thus include methoxy, ethoxy, isopropoxy, butoxy, 2-morpholinoethoxy, 3-morpholino-n-propoxy, 4-morpholino-n-butoxy, 5-morpholino-n-pentyloxy,6-morpholino-n-hexyloxy, morpholino-1-methylethoxy, morpholino-2-methylethoxy, morpholino-1-phenylethoxy, di(morpholinomethyl)methoxy, dibenzylaminoethoxy, N-phenyl-N-ethylaminoethoxy, N-(p-methoxy phenyl)-N-ethylaminoethoxy, cyanomethoxy, ethoxy-carbonylmethoxy, 3-chloro-n-propoxy, 4-chloro-n-butoxy, 5-chloro-n-pentyloxy, 6-chloro-n-hexyloxy, di(chloromethyl)methoxy, benzyloxy, phenoxy, acetoxymethoxy, dimethylamino, diethlamino methylamino or morpholino.

Where R is an acetalised formyl group, this may, for example, be formed from a lower alkanol, having 1–6 carbon atoms, e.g. methanol or ethanol, or from a glycol conveniently having 2–6, preferably 2–4, carbon atoms in the chain joining the two carbon atoms.

Where the substituent R or any other attached grouping, contains a basic nitrogen function the resulting compounds may be used as acid addition salts with physiologically acceptable mineral or organic acids e.g. hydrochloric, hydrobromic, sulphuric, phosphoric, toluene-p-sulphonic, methane sulphonic, succinic, maleic, tartaric, acetic, ascorbic, lactic, and citric acids. Where an acid grouping is present, the compounds may be used as salts with bases, e.g. alkali metal or ammonium salts or salts with physiologically acceptable amines.

The androstane anaesthetics of the invention may contain further substitution, for example at the 2α, 2β, or 16-positions and unsaturation may be present, for example as in $\Delta^{8,9}$ and/or $\Delta^1$ or $\Delta^4$ steroids. 5α-steroids are particularly preferred especially where there is a 2β-substituent or a 1,2-double bond.

Examples of substituents which may be present at position 16 include either one or two alkyl groups (especially lower (e.g. having 1–6 carbon atoms) alkyl groups, for example methyl groups), lower alkoxy groups having 1–6 carbon atoms (e.g. methoxy), or halogen atoms (e.g. fluorine or chlorine).

Examples of substituents which may be present at the 2β-position are an acyloxy group containing for example 1–9 carbon atoms, an ether or thioether group (i.e. the residue of an alcohol, a phenol or a thiol) containing for example 1–9 carbon atoms (e.g. methoxy), an alkyl or cycloalkyl group (for example containing up to 9 carbon atoms), an aryl group (e.g. a phenyl group), an aralkyl group (e.g. a benzyl group), a hydroxy group, a thiocyanato group, a nitro-oxy group, an azido group, a sulphonyloxy group (e.g. tosyloxy), or an acylthio group, or a substituted or unsubstituted amino group, e.g. a mono-or di-alkylamino or a saturated, unsaturated or aromatic heterocyclic amino group (e.g. a morpholino group), or a halogen atom (e.g. bromine).

Acyloxy substituents (which may be present at the 2β-position and may be saturated or unsaturated) include lower ($C_1-C_6$) alkanoyloxy groups, (substituted if desired, for example with one or more halogen e.g. chlorine atoms, lower alkoxy, amino and substituted amino groups), aroyloxy groups, e.g. a benzoyloxy group or aralkanoyloxy groups, e.g. a phenylacetoxy group.

Ether substituents, which may be saturated or unsaturated, include lower ($C_1-C_6$) alkoxy groups, lower alkenyloxy groups (e.g. an allyloxy group), cycloalkoxy groups, e.g. a cyclohexyloxy group, aryloxy groups, e.g. a phenoxy group and aralkoxy groups e.g. a benzyloxy group. Thioether groups corresponding to the last-mentioned oxygen groups are representative of 2β-thioether substituents.

Examples of 2β-alkyl groups include especially lower alkyl groups containing 1–5 carbon atoms such as methyl, ethyl, propyl, butyl, isobutyl and t-butyl groups. An example of a cycloalkyl group is a cyclohexyl group.

Examples of lower alkanoyloxy 2β-substituents include acetoxy, propionyloxy, butyryloxy piperidinoacetoxy, morpholinoacetoxy, diethylaminoacetoxy and chloroacetoxy groups. Examples of lower alkoxy groups include methoxy, ethoxy, propoxy, isopropoxy n-butoxy and t-butoxy groups, and the corresponding thio compounds exemplify lower alkyl thio substituents.

Lower alkoxy and lower alkylthio substituents at the 2β-position may themselves be substituted for example by one or more halogen (e.g. chlorine) atoms, lower alkoxy, esterified carboxyl (e.g. ethoxycarbonyl), hydroxy, amino or substituted amino, e.g. morpholino groups, or substituted or unsubstituted acyloxy e.g. morpholinoacetoxy, chloroacetoxy or diethylaminoacetoxy or heterocyclic groups, e.g. a tetrahydrofuranyl group. Alkyl, cycloalkyl and aryl groups may also be substituted.

Particular preferred $2\beta$-substituents are methyl, methoxy and ethoxy groups.

Examples of substituents which may be present at the $2\alpha$-position are an alkyl group, and particularly a lower alkyl group having 1–6 carbon atoms (e.g. methyl) or a halogen atom (e.g. chlorine or bromine).

As indicated above, the steroids may be unsaturated and may, for example, possess double bonds at the 8,9 and/or 1,2 or 4,5-positions.

Compounds of the invention having particularly valuable anaesthetic properties include:

$3\alpha$-hydroxy-$17\beta$-methoxycarbonyl-$5\alpha$-androstan-11-one;
$3\alpha$-hydroxy-$17\beta$-ethoxycarbonyl-$5\alpha$-androstan-11-one;
$3\alpha$-hydroxy-$17\beta$-methoxycarbonylandrost-4-en-11-one;
$3\alpha$-hydroxy-$17\beta$-dimethylcarbamoyl-$5\alpha$-androstan-11-one;
$3\alpha$-hydroxy-$17\beta$-(2'-morpholinoethoxycarbonyl)-$5\alpha$-androstan-11-one, particularly as acid addition salts with mineral or organic acids e.g. the hydrochloride and the citrate;
$3\alpha$-hydroxy-$17\beta$-cyano-$5\alpha$-androstan-11-one;
$3\alpha$-hydroxy-$2\beta$-methoxy-$17\beta$-methoxycarbonyl-$5\alpha$-androstan-11-one;
$3\alpha$-hydroxy-$17\beta$-(2'-morpholinoethoxycarbonyl)-$5\alpha$-androstan-11-one tartrate;
$3\alpha$-hydroxy-$17\beta$-methoxycarbonyl-19-nor-$5\alpha$-androstan-11-one;
$3\alpha$-hydroxy-$2\beta$-ethoxy-$17\beta$-(2'-morpholinoethoxycarbonyl)-$5\alpha$-androstan-11-one;
$3\alpha$-hydroxy-$2\beta$-ethoxy-$17\beta$-(2'-morpholinoethoxycarbonyl)-$5\alpha$-androstan-11-one citrate;
$17\beta$-cyanomethoxycarbonyl-$3\alpha$-hydroxy-$5\alpha$-androstan-11-one;
$3\alpha$-hydroxy-$17\beta$-(4'-morpholinobutoxycarbonyl)-$5\alpha$-androstan-11-one;
$17\beta$-(3'-chloropropoxycarbonyl)-$3\alpha$-hydroxy-$5\alpha$-androstan-11-one;
$3\alpha$-hydroxy-$17\beta$-(1'-methyl-2'-morpholinoethoxycarbonyl)-$5\alpha$-androstan-11-one;
$3\alpha$-hydroxy-$2\beta$-ethoxy-$17\beta$-(2'-morpholinoethoxycarbonyl)-$5\alpha$-androstan-11-one hydrochloride;
$3\alpha$-hydroxy-$17\beta$-(2'-morphlinopropoxycarbonyl)-$5\alpha$-androstan-11-one;
$3\alpha$-hydroxy-$2\beta$-ethoxy-$17\beta$-(2'-morpholinoethoxycarbonyl)-$5\alpha$-androstan-11-one mesylate;
$3\alpha$-hydroxy-$2\beta$-ethoxy-$17\beta$-(2'-morpholinoethoxycarbonyl)-$5\alpha$-androstan-11-one dihydrogen phosphate;
$3\alpha$-hydroxy-$17\beta$-cyano-$5\alpha$-androst-1-en-11-one;
$3\alpha$-hydroxy-$17\beta$(5-morpholinopentyloxycarbonyl)-$5\alpha$-androstan-11-one
$3\alpha$-hydroxy-$17\beta$-(bismorpholino methyl methoxycarbonyl)-$5\alpha$-androstan-11-one;
$17\beta$-Cyano-$3\alpha$-hydroxy-$5\beta$-androstane;
$17\beta$-Cyano-$3\alpha$-hydroxy-$5\beta$-androstan-11-one
$17\beta$-Cyano-$3\alpha$-hydroxy-$5\alpha$-androstane and
$17\beta$-Cyano-$3\alpha$-hydroxy-$5\alpha$-androst-1-ene.

The $3\alpha$-oxygenated androstane anaesthetics may be formulated as convenient, following generally known pharmaceutical practices (including both human and veterinary medical practices) with the aid of one or more pharmaceutical carriers or excipients. For anaesthetic purposes the steroids will be given by injection and thus one aspect of this invention comprises an anaesthetic composition for parenteral administration comprising a $3\alpha$-oxygenated androstane anaesthetic compound as abovedescribed in a parenterally acceptable vehicle. The composition may, for example, include one or more parenterally acceptable water-soluble substances serving to render the composition approximately isotonic with blood e.g. dextrose or glycerol.

Many of the above-described $3\alpha$-oxygenatedandrostane anaesthetic compounds are poorly soluble in water. We have found however that they may be formulated for parenteral administration in an aqueous solution of a parenterally acceptable non-ionic surface active agent.

The non-ionic surface active agents used for the purpose of this invention are generally those of the water soluble type, conveniently having an HLB value of at least 9, preferably at least about 12, advantageously at least about 13. Preferably the HLB value of the surface active agent is not greater than about 15 although it may, for example, be as high as 18. The surface active agent must naturally be one which is physiologically compatible, i.e. of itself give rise to no physiologically unacceptable side effects in the dosages employed in the intended species to be treated (man or animal). Surface active agents for use in accordance with the invention are for example to be found among the following nonionic surfactants and classes of surfactants: Polyoxyethylated derivatives of fatty (C12-C20) glyceride oils, e.g. castor oil, containing at least 35, e.g. from 35 to 45 or even up to 60 oxyethylene groups per mole of fatty oil. Polyoxyethylene ethers (containing from 10 to 30 oxyethylene groups) of long chain alcohols (containing for example from 12–18 carbon atoms).

Polyoxyethylene-polyoxypropylene ethers containing from 15 to 35 and from 15 to 30 oxyethylene and oxypropylene groups respectively. Polyoxyethylene ethers (containing from 6 to 12 oxyethylene groups) of alkyl phenols the alkyl groups of which preferably contain 6–10 carbon atoms.

Polyoxyethylated (containing from 15 to 30 oxyethylene groups) fatty acid (e.g. C12-18) esters of sugar alcohol anhydrides e.g. sorbitan or mannitan. Long-chain (e.g. C10-16) alkanoyl mono- and di-alkanolamides (the alkanol portions of which for example contain 1–5 C atoms) for example lauroyl mono- and di-ethanolamides. Polyethylene glycol esters (containing from 6 to 40 ethylene oxide units) of long chain fatty acids (containing for example 12–18 C atoms) e.g. polyethyleneglycol mono-oleate (containing for example 8 ethylene oxide units).

Examples of non-ionic surface active agents, of the foregoing types, useful in accordance with the invention include:

Cremophor EL, a polyoxyethylated castor oil containing about 40 ethylene oxide units per triglyceride unit;

Tween 80, polyoxyethylene sorbitan monooleate containing about 20 ethylene oxide units; Tween 60, polyoxyethylene sorbitan monostearate containing about 20 ethylene oxide units; and Tween 40, polyoxyethylene sorbitan monopalmitate containing about 20 ethylene oxide units.

In preferred composition according to the invention the proportion of surfactant is preferably at least 5% by weight and advantageously above 10% by weight. A very convenient proportion of surfactant has been found to be 20% by weight but 30% and up to 50% may be used. The proportions of surfactant are expressed by weight in relation to the total volume of the composition in metric units.

As will be clear, the proportion of steroid in the aqueous solution according to the invention depends upon the nature and amount of surface active agent used. The composition will contain at least 1 mg/ml of steroid and solutions can be made containing for example up to 7 mg/ml and even 10 mg/ml.

In the case of water soluble steroids, even more concentrated solutions, e.g. up to 300 mg/ml, may be prepared.

In a preferred method of preparing the solutions according to the invention the steroid is first dissolved in the selected surfactant for example, with heating and the resulting solution dissolved in water. Alternatively the steroid may be dissolved in a volatile organic solvent advantageously having a boiling point of less than about 80°C which is miscible with the surface active agent such as a volatile lower aliphatic ketone e.g. acetone or methyl ethyl ketone or a volatile halogenated hydrocarbon e.g. chloroform or methylene chloride. Acetone is particularly preferred for this purpose. The surface active agent is then added to this solution, the organic solvent removed by evaporation, for example by passing a stream of an inert gas through the solution e.g. nitrogen and the resulting solution of steroid in surfactant is mixed with water.

The solutions may also be prepared by shaking the steroid with an aqueous solution of the surface active agent.

In all cases simple tests enable one to determine the relative proportions of surface active agent required.

The anaesthetic solutions according to the invention are generally administered by intravenous injection although as is known in the anaesthetic art in certain cases, e.g. with young children intramuscular injection might be preferred.

As is usual in the case of anaesthetics, the quantity of steroid used to induce anaesthesia depends upon the weight of the individual to be anaesthetised. For intravenous administration in the average man a dose of from 0.2 to 30 mg/kg for example 0.45 to 20 mg/kg, will in general be found to be satisfactory to induce anaesthesia, the preferred dose being within the range of from 0.7 to 5 mg/kg. The dose will naturally vary to some extent dependent upon the physical condition of the patient, and the degree and period of anaesthesia required, all as is well known in the art. It is thus possible by adjustment of the dose to achieve durations of anaesthesia varying from about 10 minutes to up to an hour or more. If it is desired to maintain prolonged anaesthesia, repeated doses of the solutions of this invention may be used, such repeated doses being generally either of the same order or lower than the original dose. Alternatively continuous administration may be undertaken at for example a rate of 0.025 to 2.0 preferably 0.09–1.4 mg/Kg/Min.

Where the anaesthetic solutions are administered intramuscularly, naturally higher doses are generally necessary.

The water soluble anaesthetics do not necessarily need to be formulated in conjunction with surface active agents although in some cases such agents have been found beneficial in minimising any possibility of vein damage caused by the anaesthetic.

The new compounds according to the invention may be prepared by any convenient method, e.g., using conventional techniques. Thus it is frequently convenient first to prepare the corresponding $17\beta$-carboxylic acids. These $17\beta$-carboxylic acids may be prepared by oxidation of the $17\beta$-acetyl group of a corresponding pregnane. This oxidation may for example be effected in solution using a hypohalite salt e.g. an alkali metal or alkaline earth metal hypohalite as oxidising agent. Suitable hypohalites include, for example, sodium and potassium hypochlorites, hypobromites and hypoiodites.

The oxidation process is conveniently carried out in aqueous or non-aqueous media. Thus the reaction may for example be effected in an aqueous water-miscible organic solvent for example a water-miscible ether e.g. dioxan, tetrahydrofuran, diglyme and 1,2-dimethoxyethane or a water-miscible alcohol e.g. t-butanol. Aqueous dioxan is the preferred solvent.

The oxidation may be effected at a temperature of from −20° to 100°C, a temperature of from 5° to 10°C being preferred.

Compounds according to the invention having an esterified carboxyl group at the $17\beta$-position may be prepared from the corresponding carboxylic acid or an activated derivative, by known esterification methods.

We have found it generally convenient, particularly for the preparation of lower alkyl esters, to react the carboxylic acid with a diazoalkane, for example diazomethane or diazoethane.

The reaction with the diazoalkane is conveniently effected in solution in an inert organic solvent, for example an ether such as diethyl or tetrahydrofuran, or a lower alkanol e.g. methanol, the diazo compound itself preferably being used in solution in an inert organic solvent, for example the solvent into which it is extracted during its preparation e.g. diethyl ether. The reaction is conveniently effected at temperatures between −25°C and +30°C.

The $17\beta$-esterified carboxyl compounds according to the invention may also be prepared, for example, by reacting the corresponding $17\beta$-carboxylic acid with an alcohol or phenol in the presence of a catalyst. Acid catalysts have generally been found to be convenient e.g. sulphuric, hydrochloric, perchloric or p-toluene sulphonic acid. In one preferred method, the carboxylic acid is dissolved in an excess of the alcohol from which the ester is derived, for example, methanol, ethanol or isopropanol containing dry hydrogen chloride, advantageously at an elevated temperature, for example under reflux.

The reaction of the carboxylic acid with an alcohol from which the desired ester is derived is generally applicable to esters derived from alcohols which are liquid at ambient temperature. However, with alcohols which are normally solid at ambient temperature, the use of an activated derivative of the carboxylic acid is generally preferred. The use of a reactive derivative of the acid is not, however, limited to such alcohols and may be used for any alcohol.

Suitable activated derivatives of the $17\beta$-carboxyl compounds according to the invention include, for example, acid halides, preferably the acid chloride.

The reaction of the acid halide with an alcohol or phanol may be effected in known manner, preferably in the presence of an inert organic solvent, for example, a halogenated hydrocarbon e.g. methylene chloride or chloroform, an aromatic hydrocarbon, e.g. benzene or an ether e.g. diethyl ether or tetrahydrofuran.

In general, the reaction is preferably effected in the presence of an acid binding agent, for example, a tertiary organic base such as pyridine or triethylamine or an inorganic base such as an alkali metal carbonate or bicarbonate e.g. sodium carbonate or bicarbonate. However, when the alcohol reacted with the acid halide itself contains a basic substituent, for example an amino or substituted amino group, e.g. 2-morpholinoethanol, the basic substituent may itself act as the acid blinding agent.

The reaction of the carboxylic acid halide with the alcohol may for example be effected at temperatures between −20°C to +110°C.

The acid halides used in the above reaction may be prepared by conventional methods, for example, from the corresponding 17β-carboxylic acid by reaction with a suitable halogenating agent e.g. a thionyl, phosphoryl or oxalyl halide. When it is desired to use the acid chloride for the preparation of the esters according to the invention, thionyl chloride, phosphoryl chloride or oxalyl chloride are preferably used.

Compounds according to the invention having an ester substituent at the 17β-position may also be prepared by reacting a salt of the corresponding 17β-carboxylic acid conveniently a tertiary amine salt or quaternary ammonium salt (e.g. a trialkylamine salt or tetraalkyl ammonium salt) with an alkyl halide corresponding to the alcohol portion of the desired ester, e.g. n-butyl iodide, chloroacetonitrile, ethyl bromoacetate or acetoxy methyl chloride. This reaction is conveniently effected in a solvent medium [e.g. a lower aliphatic ketone (such as acetone or methyl ethyl ketone) or dimethyl formamide] at temperatures of from 20°–100°C.

Compounds according to the invention possessing a 17β-alkoxycarbonyl group substituted by an amino group may be prepared by first reacting the corresponding 17β-carboxylic acid with an alcohol possessing a readily eliminatable substituent (e.g. a halogen atom such as chlorine or bromine). The ester produced (which may of course be prepared by other routes) carries the readily eliminatable substituent in the ester group. The product is then reacted with ammonia or an imine (e.g. of the formula $HNR^4R^5$). Similar methods may be used to prepare other compounds wherein R is an aliphatic groups bearing an amino substituent.

The N-substituted and unsubstituted 17β-carbamoyl compounds may also be prepared by known methods. In general it has been found convenient to prepare such compounds by reacting the parent 17β-carboxylic acid, or a reactive derivative thereof, with an appropriate amine or ammonia.

Suitable activated derivatives of the carboxylic acid include, for example the corresponding acid halide e.g. the acid chloride or esters of the corresponding acid e.g. lower alkyl esters such as methyl or ethyl esters.

When an acid halide is used for the preparation of the desired amide, it is generally preferred to effect the reaction in the presence of an acid binding agent. Suitable acid binding agents include, for example, tertiary organic bases such as triethylamine or pyridine or inorganic bases such alkali metal carbonates or bicarbonates e.g. sodium carbonate or sodium bicarbonate, or, preferably an excess of the amine reactant.

The reaction is conveniently effected in a solvent which may for example be an excess of the amine used and/or an inert solvent such as a halogenated hydrocarbon e.g. methylene chloride or chloroform, an ether e.g. diethyl ether or tetrahydrofuran, or a hydrocarbon solvent e.g. benzene.

The reaction may be effected at ambient temperature although higher or lower temperatures, for example up to the boiling point of the solvent when used, may, if desired, be used.

The formation of amides from esters of the 17β-carboxylic acids by reaction with an appropriate amine or ammonia may be effected by known methods. It is generally advantageous to use as starting material a lower alkyl ester for example a methyl or ethyl ester. The reaction may conveniently be effected in a solvent such as a halogenated hydrocarbon e.g. methylene chloride or chloroform or an ether e.g. diethyl ether or tetrahydrofuran. However, an excess of the amine used in the reaction may, if desired, be used as the solvent.

In general, it is preferred to use at least a slight excess of the appropriate amine or ammonia. The reaction is effected at ambient or at an elevated temperature, for example up to the reflux temperature of the solvent when used.

Compounds according to the invention having a formyl group at the 17β-position may also be prepared by known methods.

In one such method a corresponding 20β,21-dihydroxypregnane is subjected to a glycol cleavage reaction for example by oxidation with periodic acid or a periodate or para-periodate, e.g. of an alkali metal (sodium or potassium), conveniently in an alcohol or ether solvent, e.g. methanol, ethanol, tetrahydrofuran, or dioxan or mixtures thereof with water.

Alternative methods for the preparation of 17β-formyl compounds include reduction of a corresponding 17β-carboxylic acid halide, for example using the general principle of the well-known Rosenmund reduction method. The reduction may thus be effected using catalytically activated hydrogen, the catalyst being for example, a palladium catalyst, preferably deactivated with barium sulphate and sulphur.

Acetals of 17β-formyl compounds according to the invention may be prepared for example by acid catalysed reaction of the 17β-formyl compound with the appropriate alcohol.

17β-Cyano compounds according to the invention may be prepared for example, by dehydration of the corresponding 17β-carbamoyl compounds in conventional manner, e.g. using polyphosphate ethyl ester (see Y. Kanaoka et al. Chem. Pharm. Bull. 1970 18, 397) or by reaction of the corresponding 17β-carboxylic acid with sulphamic acid (Chimia 25, 94, 1971).

The 3α-acyloxy-androstane anaesthetics may be prepared from the corresponding 3α-hydroxy-androstanes by acylation for example, in known manner. Acylation under basic conditions is generally preferred in order to avoid undesired side reactions.

The acylating agent may for example be the anhydride or halide (preferably the chloride) of the corresponding carboyxlic acid. In general, the acylation is effected in the presence of a tertiary organic base such as pyridine, 4-methylpyridine or N-methylmorpholine.

The acylation is generally effected in a solvent, preferably an aprotic solvent, which may, for example, be an excess of the acylating agent and/or an excess of a tertiary organic base, if desired in the presence of a co-solvent, for example tetrahydrofuran.

We have found that the 3α-oxygenated-Δ⁴-androstane anaesthetics of the invention are conveniently prepared by nucleophilic displacement of the 3β-substituent in a corresponding member of the more readily available 3β-oxygenated steroids.

The 3β-substituent in the 3β-steroid used in this process should be one capable of nucleophilic displacement by a hydroxyl group or acyloxy group and thus the 3β-steroid will contain at the 3-position an allylically replaceable substituent in the β-configuration such as a 3β-hydroxy group, an ether, carboxylic ester or sulphonyloxy ester of such a 3β-hydroxy group or a halogen atom (e.g. chlorine or bromine). Esters of the 3β-hydroxy group are conveniently acyl or sulphonyl esters, the acyl esters generally containing at least one electron-withdrawing substituent whereby displacement of the acyloxy group is facilitated. Acids which may be used for the preparation of such allylic acyl esters are preferably α-substituted acetic acids or nuclear substituted benzoic acids, in each case at least one substituent being electron-withdrawing. Specific examples of suitable acids include haloacetic acids, methoxyacetic acid, alkylthioacetic acids, cyanoacetic acid, glyoxylic acid, phenylglyoxylic acid, substituted phenylglyoxylic acids e.g. substituted by one or more halogen atoms (F,Cl, Br or I), methoxy groups or methyl groups or benzoic acids substituted by 4-methyl, 2- or 3-chloro or bromo, 2-, 3- or 4-nitro or 3,5-dinitro, 2-, 3- or 4-trifluoromethyl, 2-carbamoyl, 2-, 3- or 4-esterified carboxyl or 4-cyano substituents.

3β-Sulphonyloxy steroids which may be used for preparing the 3α-hydroxy compounds according to the invention are conveniently esters of alkyl or aryl sulphonic acids. Methane sulphonic acid and p-toluene-sulphonic acid are preferred sulphonic acids.

The preferred 3β-substituent for use in the hydrolysis reaction is a 3β-dichloroacetyl group.

For the preparation of 3α-hydroxy compounds, generally the displacement reaction will be a hydrolysis reaction and may be conveniently effected in aqueous solution, preferably at a pH of from 4 to 8, advantageously at a pH of about 5. In order generally to improve the solubility of the steroids present in the reaction medium, a water miscible organic solvent may be used, e.g. acetone or tetrahydrofuran.

The reaction mixture may be buffered to maintain the pH thereof within the desired limits, preferred buffer systems including known phosphate, borate, acetate and formate buffer systems.

Instead of using a buffer system, adjustment of the pH from time to time with a weak alkali, e.g. aqueous sodium bicarbonate may be used.

The hydrolysis may be effected at ambient temperature, although elevated temperatures e.g. the reflux temperatures of the reaction medium is generally preferable.

In another method of carrying out the desired hydrolysis employing a non-buffered system, the 3β-steroid is subjected to hydrolytic displacement in an aqueous solution of a strongly polar organic solvent, e.g. dimethyl formamide, dimethyl acetamide or N-methyl pyrrolidine. This reaction is advantageously effected at elevated temperatures e.g. between 75°C and the reflux temperature of the solvent used.

The 3β-substituted-Δ⁴-androstanes used in the preparation of 3α-oxygenated-Δ⁴-androstane steroids according to the invention may be prepared by known methods. 3β-Oxygenated-Δ⁴androstanes of this type may conveniently be prepared, for example, by reduction of the corresponding 3-oxo-Δ⁴-androstanes and if desired subsequent acylation of the 3β-hydroxy-Δ⁴-androstane produced.

The 3α-oxygenated 5α-androstane anaesthetics according to the invention may, for example, be prepared from the corresponding 3β-hydrocarbonsulphonyloxy-5α-androstan-11-one in a manner analogous to that described by Nagata et al (Helv. Chim.Acta, 1959, 42, 1399) by reaction with a carboxylic acid or a salt thereof whereby a 3α-acyloxy 5α-androstane is formed. Where the 3α-hydroxy steroid is required, the 3α-acylate may, for example, be submitted to basic hydrolysis.

5α-Steroids according to the invention having a 3α-hydroxy group may also be prepared from the corresponding 3-oxo compound by stereospecific reduction, e.g. using an iridium catalyst.

The iridium reduction is preferably carried out by first preparing an iridium catalyst reduction system from an iridium salt or acid (e.g. chloroiridic acid), an ester of phosphorous acid (e.g. trimethyl phosphite), water, and an organic reaction medium (e.g. an alcohol such as isopropanol). This reduction system is then preferably neutralised with an organic base (e.g. triethylamine), and reacted with the steroid.

The 5β-steroids may similarly be prepared by hydride reduction of 3-oxo steroids.

Compounds according to the invention having a 3α-oxygenated-5α-androst-1-ene structure may be prepared by known methods, preferably -androst-1-ene dehydros halogenation of the corresponding 3α-oxygenated-2β-halo-5α-androstane compounds, for example, the 2β-bromo compounds.

The dehydrohalogenation may be effected, for example, using a nitrogen containing Lewis base such as a di-lower alkyl lower acylamide e.g. dimethylformamide or dimethylacetamide advantageously in the presence of an alkali metal or alkaline earth metal carbonate, for example calcium carbonate.

In general it has been found convenient to effect the dehydrohalogenation at an elevated temperature for example from 80° to 170°C.

The above-described dehydrohalogenation may be effected, for example, using 3α-hydroxy-2β-halo-5α-androstanes or protected derivatives thereof such as 3α-esters or tetrahydropyranyl ethers. When it is desired to prepare a 3α-hydroxy-5α-androst-1-ene from a 3α-acyloxy-2β-halo-compound it may be convenient, for example first to prepare the corresponding 3α-acyloxy-5α-androst-l-ene and subsequently to convert the 3α-acyloxy group thereof into a 3α-hydroxy group by known methods. In one method, solvolysis is effected by reaction with a lower alkanol, for example methanol or ethanol, or with water in the presence of an acid or of a base such as an alkali metal hydroxide, carbonate or bicarbonate for example potassium or sodium hydroxide, carbonate or bicarbonate. The lower alkanol may conveniently serve as an organic solvent for the reaction; the reaction is preferably effected at a temperature of 15°–40°C when an alkali metal hydroxide is used as the base and preferably at a temperature of 50°–100°C when an alkali metal carbonate or bicarbonate are used as the base. Lower temperatures may be employed by using added lithium halide or calcium halide.

It is particularly useful to protect the 3α-hydroxy group during the dehydrohalogenation reaction by formation of a 3α-tetrahydropyranyl ether, e.g. by reaction with dihydropyran and a source of protons, e.g. an acid such as p-toluene sulphonic acid. This ether group may readily be removed selectively without attack at a 17β-ester.

3β-Methyl-3α-hydroxy steroids according to the invention may be prepared by reduction of corresponding spiro-2′-oxiranes with a complex metal hydride. The metal hydride may, for example be lithium aluminium hydride; where the 11-oxo group is reduced by the hydride the 11-hydroxy group can be re-oxidised, e.g. by chromic acid. These reactions can also be effected in corresponding pregnanes which may then be subjected to oxidation to 17β-carboxylic acids as described above. and thence converted into compounds of the invention.

Compounds according to the invention having a 2α,2β or 16 substituent or a double bond at the 1,2,4,5 or 8,9 positions may be prepared, for example, by one of the above-described processes using an appropriately substituted or unsaturated compound.

Alternatively, 2β-substituted compounds in the 5α-series may be prepared by way of the corresponding 2α,3α-epoxy compound. The epoxy compound itself may be prepared by first dehydrating a 3α-hydroxy compound to give the corresponding $\Delta^2$ compound (e.g. by first tosylating the hydroxy group and then removing the elements of p-toluene sulphonic acid from the product), and then treating the $\Delta^2$ compound with a peracid to form the 2α,3α epoxide ring. A 2β-substituent, Z, may then be introduced and the 3α-hydroxy group regenerated by reacting the epoxy compound with a compound of the formula ZH or a compound furnishing an anion Z and a cation, followed, where a metal derivative of the 3α-hydroxy group is first formed, by treatment with a source of protons.

Compounds having a 16α-alkyl group may also be prepared by reacting a corresponding $\Delta^{16}$-steroid with a lithium dialkyl cuprate, preferably in the presence of an etheric solvent (e.g. diethyl ether). This reaction may, if desired, be effected simultaneously with the introduction of a 2β-alkyl group by reacting the 2α,3α-epoxy-$\Delta^{16}$ steroid with the lithium reagent.

In various of the transformations herein described, as will be clear to those skilled in the art, it may be necessary to protect a 3α-hydroxy group if such is present. Thus, for example, it may be necessary in oxidation reactions and during conversions of a 17β-carboxylate group to an acid halide group. Such temporary protection may be effected in known manner, e.g. by formation of a 3α-ester group which may be readily re-converted to a free hydroxy group. Lower alkanoyl groups are frequently very satisfactory and may be removed by hydrolysis. For many purposes we have found that temporary protection of the 3α-hydroxy group by formation of a nitrate ester thereof is especially convenient. 3α-Nitro-oxy groups may be readily converted to 3α-hydroxy groups by catalytic hydrogenation or by chemical reduction with for example a metal/acid system, such as zinc and acetic acid. The 3α-hydroxy group may also be protected in the form of an ether, a tetrahydropyranyl ether.

The following Examples are given by way of illustration only. All temperatures are in degrees Celsius. The term petrol as used herein refers to petroleum ether (b.p. 60°–80°).

"Stock" chloroiridic acid was prepared by refluxing a mixture of chloroiridic acid (0.09 g), 90% isopropyl alcohol (200 ml.) and trimethyl phosphite (16 ml.) for 16 hr. The solution was neutralised with triethylamine prior to use.

Rotations were determined in chloroform at about 1% W/V concentration unless otherwise stated. Preparative thin layer chromatography (t.l.c.) was carried out on silica gel.

EXAMPLE 1

3α-Hydroxy-17β-methoxycarbonyl-5α-androstan-11-one

A solution of 3α-hydroxy-11-oxo-5α-androstane-17β-carboxylic acid (350 mg.) in methanol (20 ml.) and ether (10 ml.) was treated with a dry ethereal solution of diazomethane. After 10 minutes, any unreacted diazomethane was destroyed by the addition of a drop of glacial acetic acid and the mixture was evaporated to small bulk. This was taken up in ether and washed with dilute sodium hydrogen carbonate solution, with water, dried and evaporated to a foam. The product was crystallised from acetone and petrol to give title compound (28/ mg.) as off white needles; m.p. 162 163°; $[\alpha]_D + 77°$.

EXAMPLE 2

17β-Ethoxycarbonyl-3α-hydroxy-5α-androstan-11-one

A solution of 3α-hydroxy-11-oxo-5α-androstane-17β-carboxylic acid (500 mg.) in dry ethanol containing 3.3%, by weight, of hydrogen chloride (100 ml.) was refluxed for 2 hours.

The solution was evaporated to small volume, diluted with ether, washed with saturated sodium hydrogen carbonate solution, with water, dried and evaporated to a foam, which was crystallised from acetone and petrol to give title compound (380 mg.) as colourless needles; m.p. 105°–107°; $[\alpha]_D + 63°$.

EXAMPLE 3

3α-Hydroxy-17β-isopropoxycarbonyl-5α-androstan-11-one

A solution of 3α-hydroxy-11-oxo-5α-androstane-17β-carboxylic acid (550 mg.) in dry isopropanol containing 3.7%, by weight, of hydrogen chloride (100 ml.) was refluxed for 6½ hours.

The solution was evaporated to small volume, diluted with ether, washed with saturated sodium hydrogen carbonate solution, with water, dried and evaporated to a foam, which was purified by preparative t.l.c. to give title compound (540 mg.) as a white foam; $[\alpha]_D + 73°$

EXAMPLE 4

3α-Hydroxy-2β-methoxy-17β-methoxycarbonyl-5α-androstan-11-one

2α,3α-Epoxy-5α-pregnane-11,20-dione (200 mg) was dissolved in dry methanol (20 ml), and concentrated sulphuric acid (0.1 ml.) was added. The solution was stirred at room temperature for 20 minutes, and then poured into water (125 ml.) to give a white crystalline precipitate which was filtered off and dried in vacuo over phosphorus pentoxide to give 3α-hydroxy-2β-methoxy-5α-pregnane-11,20-dione (175 mg.), m.p. 163°–164°, $[\alpha]_D + 109°$.

A solution of the above product (1.4 g.) in dioxan (55 ml.) and water (16 ml.) was stirred and cooled to 8°.

Sodium hypobromite solution (30 ml.), prepared as described in preparation 7, was added and the mixture stirred for 3 hours, between 5° and 10°.

Sodium sulphite heptahydrate (0.8 g.) in water (5 ml.) was added and the mixture refluxed for 15 minutes. The hot solution was acidified with concentrated hydrochloric acid (2.5 ml.) filtered, evaporated to small volume and extracted with chloroform. The extract was washed with water, dried and evaporated to leave a solid residue of impure 3α-hydroxy-2β-methoxy-11-oxo-5α-androstane-17β-carboxylic acid.

The total product was dissolved in methanol (30 ml.) and ether (30 ml.) and treated with an ethereal solution of diazomethane. After 10 minutes a drop of glacial acetic acid was added. The solution was evaporated under reduced pressure to leave a solid residue, which after purification by preparative t.l.c. and crystallisation from ethyl acetate and petrol gave title compound (300 mg.) as off-white needles; m.p. 182°–186°; $[\alpha]_D$ + 73°

EXAMPLE 5

3α-Hydroxy-2β-methoxy-17β-methoxycarbonyl-5α-androstan-11-one

2α,3α-Epoxy-17β-methoxycarbonyl-5α-androstan-11-one (500 mg.) in warm dry methanol (30 ml.) was treated with concentrated sulphuric acid (0.15 ml.). After 30 minutes the solution was poured into stirred water. The precipitated product was isolated, washed with water and dried over sodium hydroxide in vacuo to give fairly pure title compound (420 mg.) as a white powder; m.p. 170°–182°; $[\alpha]_D$ + 68°,

EXAMPLE 6

2β-Bromo-3α-hydroxy-17β-methoxycarbonyl-5α-androstan-11-one

2α,3α-Epoxy-17β-methoxycarbonyl-5α-androstan-11-one (500 mg.) in chloroform (32 ml.) was stirred with 48% aqueous hydrogen bromide (10 ml.). After an hour the mixture was washed with an excess of aqueous sodium bicarbonate and with water, was dried (MgSO$_4$) and evaporated to a froth (628 mg.) Crystallisation from ethyl acetate/light petroleum afforded title compound (330 mg.) as colourless needles; m.p. 205°–208°; $[\alpha]_D$ + 76°,

EXAMPLE 7

17β-Formyl-3α-hydroxy-5α-androstan-11-one

A solution of 3α,20β,21-trihydroxy-5α-pregnan-11-one (400 mg.) in methanol (30 ml.) was stirred with sodium m-periodate (250 mg.) in water (3 ml.) for 18 hours.

The mixture was diluted with chloroform, washed with water, dried and evaporated to a foam, which was crystallised from benzene, acetone and petrol to give title compound (80 mg.) as colourless crystals; m.p. 226°–230°; $[\alpha]_D$ + 73°,

EXAMPLE 8

3α-Hydroxy-17β-dimethoxymethyl-5α-androstan-11-one

A solution of 21-acetoxy-3α-hydroxy-5α-pregnane-11,20-dione (1 g), in methanol (100 ml.) was stirred under nitrogen with a 10% aqueous solution of potassium hydrogen carbonate (4 ml.) for an hour.

The mixture was neutralised with glacial acetic acid and evaporated under reduced pressure. The residue was dissolved in chloroform, washed with water, dried and evaporated to give 3α,21-dihydroxy-5α-pregnane-11,20-dione.

This was dissolved in ethanol (50 ml.) and stirred with sodium borohydride (110 mg.) in water (5 ml.) for 40 minutes. A little glacial acetic acid was added and the solvents evaporated to small volume. The mixture was poured into water and extracted with chloroform. The extract was washed with water, dried and evaporated to leave 3α,20β,21-trihydroxy-5α-pregnan-11-one.

This was dissolved in methanol (50 ml) and stirred with sodium m-periodate (550 mg.) in water (3 ml.) for 43 hours. The mixture was extracted into chloroform, washed with water, dried and evaporated to leave crude 17β-formyl-3α-hydroxy-5α-androstan-11-one as a foam.

The foam was dissolved in methanol (10 ml.) and toluene-p-sulphonic acid (2 mg.) was added. The mixture was warmed and left to stand at room temperature for 24 hours. Pyridine (2 drops) was added and the mixture evaporated to a residue which was purified by column chromatography, on alumina. The product was crystallised from ethyl acetate and petrol containing a little pyridine to give title compound (177 mg.) as colourless crystals; m.p. 136°–142°; $[\alpha]_D$ + 47°

EXAMPLE 9

3α-Hydroxy-17β-(2′-N-morpholinoethoxycarbonyl)-5α-androstan-11-one, citrate

A solution of 3α-hydroxy-17β-(2′N-morpholinoethoxycarbonyl)-5α-androstan-11-one (89.5 mg.) in ethanol (1 ml.) was treated with 0.1 M citric acid (2 ml.). The ethanol was evaporated off and the resultant solution freeze dried to leave a white powder. Water (5 ml.) was added and the solution filtered. The filtrate was diluted with water to give a solution of 3α-hydroxy-17β-(2′-N-morpholinoethoxycarbonyl)-5α-androstan-11-one, citrate at a concentration of 10 mg./ml. with respect to steroid. Similarly aqueous solutions were prepared in concentrations of 10 mg/ml. with respect to the steroid 3α-Hydroxy-17β-(2′N-morpholinoethoxycarbonyl) 5α-androstan-11-one, hydrochloride and tartrate using 0.1N hydrochloric acid and 0.1M tartaric acid in place of 0. 1M citric acid.

EXAMPLE 10

3α-Hydroxy-17β-methoxycarbonyl-11-oxo-5α-androstane 3-hemisuccinate

A solution of 3α-hydroxy-17β-methoxycarbonyl-5α-androstan-11-one (400 mg.) and succinic anhydride (400 mg.) in anhydrous pyridine (10 ml.) was allowed to stand at room temperature for 21 hours. The mixture was heated at 100° for 8 hours. The reaction was still incomplete and the mixture was refluxed for 5 hours. The solution was poured into iced water, acidified with hydrochloride acid and extracted with chloroform. The chloroform was washed with water, dried (Na$_2$SO$_4$) and evaporated to a foam. Purification by preparative TLC gave title compound (175 mg.) as a white foam, $[\alpha]_D$ + 66.5°.

EXAMPLE 11

17β-Carbamoyl-3α-hydroxy-5α-androstan-11-one

17β-chlorocarbonyl-3α-nitro-oxy-5α-androstan-11-one (prepared from the corresponding 17β-carboxylic acid (1 g) as described in preparation 5) was shaken with 880 ammonia (8 ml.), benzene (5 ml and water (5 ml.) for 5 minutes. After 18 hours the precipitate was filtered, washed with water and dried. Crystallisation from ethyl acetate and petrol gave 17β-carbamoyl-3α-nitro-oxy-5α-androstan-11-one (520 mg.) as colourless needles, m.p. 193°–196°, $[\alpha]_D + 53°$ A solution of the above 3-nitrate (400 mg.) in glacial acetic acid (10 ml.) was stirred with zinc powder (1.2 g.) for 1½ hours. The mixture was filtered and the zinc washed with chloroform. The combined filtrates were washed with water, dried ($Na_2SO_4$) and evaporated to a residue crystallisation from ethyl acetate and petrol gave title compound (190 mg.) as colourless rods; m.p. 242°–250° (dec), $[\alpha]_D + 54°$

EXAMPLE 12

3α-Hydroxy-17β-N-methylcarbamoyl-5α-androstan-11-one

17β-chlorocarbonyl-3α-nitro-oxy-5α-androstan-11-one (954 mg.) in dry ether (20 ml.) and dry methylene chloride (20 ml.) was treated with 25% aqueous solution of methylamine (6 ml.). After 18 hours, the mixture was evaporated and a solution of the residue in ether and ethyl acetate was washed with water, dried ($Na_2SO_4$) and evaporated to a foam. Crystallisation from ether and chloroform gave 17β-N-methylcarbamoyl-3α-nitro-oxy-5α-androstan-11-one (525 mg.), m.p. 184°–186°, $[\alpha]_D + 51.5°$ A solution of the above 3-nitrate (400 mg,) in glacial acetic acid (10 ml.) was stirred with zinc powder (1.5 g.) at 16° for 1¼ hours. The mixture was filtered and the zinc washed with chloroform. The combined filtrates were washed with water, saturated sodium bicarbonate solution and again with water, dried ($Na_2SO_4$) and evaporated to a foam. Crystallisation from ethyl acetate and petrol gave title compound (230 mg.) as colourless plates; m.p. 229°–234°, $[\alpha]_D + 51°$.

EXAMPLE 13

3α-Hydroxy-17β-N,N-dimethylcarbamoyl-5α-androstan-11-one

17β-chlorocarbonyl-3α-nitro-oxy-5α-androstan-11-one (prepared from the corresponding 17β-carboxylic acid (1g) as described in Preparation 5) in dry ether (20 ml.) was treated with a solution of dimethylamine (6 ml.) in dry ether (10 ml.). After 18 hours the mixture was diluted with ether, washed with water, dried ($Na_2SO_4$) and evaporated to a foam. Crystallisation from ethyl acetate and petrol gave 17β-N,N-dimethylcarbamoyl-3α-nitro-oxy-5α-androstan-11-one (560 mg.) as off-white rods, m.p. 172°–176°, $[\alpha]_D + 45.9°$ A solution of the above 3-nitrate (360 mg.) in glacial acetic acid (10 ml.) was stirred with zinc powder (1.2 g.) for 1¼ hours. The mixture was filtered and the zinc washed with chloroform. The combined filtrates were washed with water, saturated sodium bicarbonate solution and again with water, dried ($Na_2SO_4$) and evaporated to a foam. Crystallisation from ethyl acetate and petrol gave title compond (198 mg.) m.p. 215°–221°, $[\alpha]_D + 33°$.

EXAMPLE 14

3α-Hydroxy-17β-methoxycarbonylandrost-4-en-11-one

17β-Methoxycarbonylandrost-4-ene-3,11-dione (2.8 g.) was dissolved in dry methanol (250 ml.) and to the stirred solution was added sodium borohydride (600 mg.) in portions over 2 hours. The reaction was then left to stand for 30 minutes, and then concentrated by evaporation under reduced pressure and poured on to ice. The precipitate was extracted into chloroform and the organic solution was dried over sodium sulphate and evaporated to an oil which was purified by preparative TLC to give 3β-hydroxy-17β-methoxycarbonylandrost-4-en-11-one (506 mg.) as colourles plates, m.p. 197°–201°, $[\alpha]_D$ 30 144°.

The above product (500 mg.) was dissolved in dry methylene chloride (10 ml.) and to the solution was added pyridine (0.20 ml.) and dichloroacetyl chloride (0.24 ml.). The yellow solution was stirred at room temperature for 45 minutes, and then diluted with methylene chloride, washed with water, dried over sodium sulphate and evaporated to give the crude dichloroacetate as an oil.

This crude ester (about 600 mg.) was dissolved in acetone (50 ml.) and pH 5 acetate buffer was added. The solution was refluxed for 45 minutes, then concentrated by evaporation under reduced pressure, diluted with water and extracted with chloroform. The organic solution was dried over sodium sulphate and evaporated to an oil which was purified by preparative TLC and recrystallisation of the main band from acetone/petrol to give title compound (176 mg.) as off-white prisms, m.p. 121°–125°, $[\alpha]_D + 215°$.

EXAMPLE 15

17β-Cyano-3α-hydroxy-5α-androstan-11-one ;

17β-Carbamoyl-3α-nitro-oxy-5α-androstan-11-one (907 mg.) and polyphosphate ester (7.26 g.) [prepared by the method of Y. Kanaoka etal, Chem.Pharm. Bull., 1965,13,1065] were refluxed in chloroform (50 ml.) for four hours. The solvent was evaporated and the residue was stirred with 30% aqueous sodium carbonate (15 ml.) for an hour. The mixture was extracted with ether and the extract washed with water, dried ($Na_2SO_4$) and evaporated to give a residue which was taken up in chloroform, filtered through a column of silica gel and recrystallised from chloroform/ether to give 17β-cyano-3α-nitro-oxy-5α-androstan-11-one (610 mg.) as colourless needles; m.p. 208°–214°, $[\alpha]_D + 79°$.

The above 3-nitrate (499 mg.) in glacial acetic acid (15 ml.) and tetrahydrofuran (10 ml.) was stirred with zinc powder (1g.) for an hour at room temperature. The zinc was removed, washed with chloroform and the combined filtrates were washed with water, with aqueous sodium bicarbonate (50 ml.) and again with water dried ($Na_2SO_4$) and evaporated to a froth (446 mg.). Crystallisation from ether/petroleum ether gave title compound (246 mg.) as colourless needles, m.p. 256°–262°; $[\alpha]_D + 74°$.

EXAMPLE 16

17β-N,N-Diethylcarbamoyl-3α-hydroxy-5α-androstan-11-one

17-Chlorocarbonyl-3α-nitro-oxy-5α-androstan-11-one (946 mg.) in ether (30 ml.) methylene chloride (20 ml.) and diethylamine (1 ml.) was left overnight at room temperature. Ether was added and the mixture was washed with water dried ($Na_2SO_4$) and evaporated to give a residue which on recrystallisation from ethyl acetate/petroleum ether gave 17β-N,N-diethylcarbamoyl-3α-nitro-oxy-5α-androstan-11-one (485 mg.) as colourless rods, m.p. 168°–173°; $[\alpha]_D$ + 41.5°.

The above 3-nitrate (381 mg.) in glacial acetic acid (10 ml.) was stirred with zinc powder (1g.) for an hour at room temperature. The zinc was removed, washed with chloroform and the combined filtrates were washed with water, with aqueous sodium bicarbonate (50 ml.) and again with water, dried ($Na_2SO_4$) and evaporated to give title compound (268 mg.) as white forth; $[\alpha]_D$ + 26°.

EXAMPLE 17

17β-Morpholinocarbonyl-3α-hydroxy-5α-androstan-11-one

17β-chloro-carbonyl-3α-nitro-oxy-5α-androstan-11-one (820 mg.) in dry ether (25 ml.) and dry methylene chloride (10 ml.) was treated with morpholine (3 ml.) at room temperature. After two hours the solution was diluted with chloroform, washed with water, dried ($Na_2SO_4$) and evaporated to a foam (855 mg.). Crystallisation from ethyl acetate gave 17β-Morpholinocarbonyl-3α-nitro-oxy-5α-androstan-11-one (622 mg.) as colourless needles, m.p. 201°–207°; $[\alpha]_D$ + 32°.

A solution of the above 3-nitrate (400 mg.) in glacial acetic acid (10 ml.) was stirred with zinc powder (1g.) at room temperature for 1½ hours. The mixture was filtered and the zinc washed with chloroform. The combined filtrates were washed with water, saturated sodium bicarbonate solution and again with water, dried ($Na_2SO_4$) and evaporated to a foam. Crystallization from acetone and ether gave title compound (264 mg.) as colourless needles; m.p. 210°–212°; $[\alpha]_D$ + 15°.

EXAMPLE 18

17β-n-Butoxycarbonyl-3α-hydroxy-5α-androstan-11-one

A solution of 3α-hydroxy-11-oxo-5α-androstane-17β-carboxylic acid (521 mg.) in dry acetone (50 ml.) was refluxed with triethylamine (1.04 ml.) and n-butyl iodide (0.87 ml.) for 16 hours. The mixture was evaporated to a residue which was dissolved in chloroform, washed with water, dried ($Na_2SO_4$) and evaporated to a foam (534 mg.). A solution of the foam in ether was washed with saturated sodium bicarbonate solution and with water, dried ($Na_2SO_4$) and evaporated to give title compound (443 mg.) as a white foam, $[\alpha]_D$ + 51°.

EXAMPLE 19

17β-Acetoxymethoxycarbonyl-3α-hydroxy-5α-androstan-11-one

3α-Hydroxy-11-oxo-5α-androstane-17β-carboxylic acid (1g.) was warmed with tetra-butyl ammonium hydroxide (1.94g. Of 40% solution) and acetone (10 ml.) to effect solution. The solution was refluxed with sodium iodide (100 mg.). potassium bicarbonate (150 mg.) and chloromethyl acetate (0.6 ml.) for 2 hours. The mixture was evaporated to small volume, diluted with ethyl acetate, washed with water, dried ($Na_2SO_4$) and evaporated to a residue. Purification by preparative t.l.c. gave title compound (less polar band) (318 mg.) as white foam; $[\alpha]_D$ + 52°.

EXAMPLE 20

Preparation of 17β-alkoxycarbonyl-3α-hydroxy-5α-androstan-11-ones (Table 1)

Stage 1:
17β-chlorocarbonyl-3α-nitro-oxy-5α-androstan-11-ones

3α-Nitro-oxy-5α-androstan-11-one 17β-carboxylic acid and oxalyl chloride (ca. 2.5 ml./g. of steroid) were refluxed in dry benzene (30 – 100 ml./g. of steroid) for ca. 2 hours. Evaporation to dryness afforded the title compound which was used directly in the next stage.

Stage 2:
17β-Alkoxycarbonyl-3α-nitro-oxy-5α-androstan-11-ones

A solution of 17β-chlorocarbonyl-3α-nitro-oxy-5α-androstan-11-one and the appropriate alcohol (ROH) in dry ether (ca. 15 ml./mmole of steroid) were stirred at room temperature overnight. The reaction mixture was washed with aqueous 2% sodium hydroxide and the aqueous phase was extracted with chloroform. The chloroform extract was washed with water, dried ($MgSO_4$), filtered and evaporated to afford a crude product which was purified by preparative t.l.c..

Stage 3:
17β-Alkoxycarbonyl-3α-hydroxy-5α-androstan-11-ones

Zinc dust (2–3g./g. of steroid) was added to a stirred solution of 17β-alkoxycarbonyl-3α-nitro-oxy-5α-androstan-11-one dissolved in glacial acetic acid (ca. 15 ml./g. steroid). After 15 min. the reaction mixture was diluted with chloroform, neutralised to pH 6 with aqueous 10% sodium carbonate, and filtered. The chloroform layer was separated, washed with water and dried ($MgSO_4$). Filtration and evaporation afforded the title compound as a froth which could be purified by preparative t.l.c.

TABLE I.

Preparation of 17β-alkoxycarbonyl-3α-hydroxy-5α-androstan-11-ones.

| R | Stage 1 Starting Material mmole | Stage 2 Starting Material g. | ROH mmole | Pure % Yd. | Product $[\alpha]_D$ | C.% | Stage 3 Starting Material mmole | % Yd. | Product $[\alpha]_D^{26}$ | C.% |
|---|---|---|---|---|---|---|---|---|---|---|
| —$CH_2CH_2N(CH_2\phi)_2$ | 2.5 | 0.98 | 7.5 | 23[1] | +39 | 1.0 | 0.5[2] | 85[3] | +36 | 1.0 |
| —$CH_2CH_2N\overset{\phi}{\underset{Et}{\diagdown}}$ | 5.3 | 2.2 | 15[4] | 40 | +55 | 0.4 | ca.4.7[5] | 38[6,13] | +39 | 0.4 |

TABLE I.-continued

Preparation of 17β-alkoxycarbonyl-3α-hydroxy-5α-androstan-11-ones.

| R | Stage 1 Starting Material mmole | Stage 1 Starting Material g. | Stage 2 ROH mmole | Stage 2 Pure % Yd. | Stage 2 Product $[\alpha]_D$ | Stage 2 C.% | Stage 3 Starting Material mmole | Stage 3 % Yd. | Stage 3 Product $[\alpha]_D^{26}$ | Stage 3 C.% |
|---|---|---|---|---|---|---|---|---|---|---|
| -CH₂CH₂N(C₆H₄-OCH₃)(Et) | 4.1 | 1.75 | ca.10[7] | 55 | +50 | 1.5 | 1.8[2] | 80[3] | +40 | 1.0 |
| -CH₂CHN(Me)(morpholino) | 4.0 | 1.55 | 4.2[8] | 18[9] | +52.5 | 0.48 | 0.6[2,9] | 65[3] | +44 | 0.7 |
| -CHCH₂N(Me)(morpholino) | 4.0 | 1.65 | ca.14 | [A] 25[10] — [B] 18[10] — | — — | — — | 0.48[2] 0.42[2] | 44[3] 93[3] | +82 +44 | 0.3 0.5 |
| -CHCH₂N(C=O)(morpholino) | 4.0 | 1.55 | 5.0[8] | [A] 44[10] [B] 30[10] | +83.5 +37 | 0.5 0.5 | 0.80[2] 0.53[2] | 78[3] 75[3] | +80 +31 | 1.0 0.5 |
| -⌬ (phenyl) | 9.0 | 3.5 | 21[11] | 77[12] | +98 | 0.7 | 4.7[2] | 46[3,13] | +94 | 0.6 |
| -CH₂CH₂N(piperidino) | 0.89 | 0.32 | 15[14] | 23 | +51.5 | 1.0 | 4.9[2] | 100[13] | +43 | 1.0 |
| -CH₂CH₂N(pyrrolidino) | 2.6 | 0.82 | 10[14] | 37 | +54 | 0.8 | 0.9[2] | 73[13] | +47 | 1.1 |

NOTES TO TABLE I
1. Wt. of insoluble steroid remaining after trituration with petrol to remove 2¹-N,N-dibenzylaminoethanol.
2. Pure.
3. % Yield with respect to pure nitrate ester.
4. Reaction incomplete overnight. A further portion of 2-N,N-ethylanilinoethanol (2.5g., 15 mmole) was added and the reaction mixture was stirred at room temperature for a further 4.5 hr.
5. Crude nitrate ester from preceding step.
6. % Yield with respect to pure 3α-nitro-oxy-5α-androstan-11-one 17β-carboxylic acid.
7. Reaction incomplete overnight. A further portion of 2-N,N-ethyl p-methoxyanilinoethanol (4.5 mmole) was added and the reaction mixture was stirred at room temperature for a further 2 hr.
8. Dry pyridine was added to remove hydrogen chloride.
9. Mixture of diastereoisomers.
10. Single diastereoisomer.
11. Reagent was added as a suspension in dry pyridine (5 ml.).
12. During extraction of the nitrate ester, chloroform or ethyl acetate was added to dissolve precipitated organic material. The crude product was purified by crystallisation from chloroform/ether.
13. The neutralisation to pH 6 was omitted from the work-up but the chloroform extract was washed with aqueous 10% sodium bicarbonate.
14. Methylene chloride was added as co-solvent (10–20 ml./g.).

EXAMPLE 21

Preparation of 3α-hydroxy-17β-morpholinoalkoxycarbonyl-5α-androstan-11-ones.

(Table II)

Stage 1:

17β-chloroalkoxycarbonyl-3α-nitro-oxy-5α-androstan-11-ones

3α-Nitro-oxy-5α-androstan-11-one 17β-carboxylic acid and oxalyl chloride (ca. 2.5 ml./g. of steroid) were refluxed in dry benzene (ca. 37 ml./g. of steroid) for 2 hr. and then evaporated to dryness. The residue was dissolved in a mixture of dry ether (ca. 20ml./mmole of steroid) and dry pyridine (ca. 2 ml./g. of steroid). The chlorohydrin (R₁OH, 4 mmole./g. of steroid) was added and the reaction mixture stirred at room temperature for 2 hr. before being washed with water, saturated aqueous sodium chloride solution, dried, filtered and evaporated to give the title compound as a residue which was purified either by recrystallisation or by preparative t.l.c.

Stage 2:

3α-Hydroxy-17β-morpholinoalkoxycarbonyl-5α-androstan-11-ones

A mixture of 17β-chloroalkoxycarbonyl-3α-nitro-oxy-5α-androstan-11-one and morpholine (ca. 5 ml./g.) was gently refluxed (½ – 1 hr.) and then cooled and poured into aqueous sodium bicarbonate. Extraction with chloroform followed by the usual work-up procedures afforded the 17β-morpholinoalkoxycarbonyl-3α-nitro-oxy-5α-androstan-11-one as a gum. The crude nitrate was dissolved in glacial acetic acid (ca. 15ml./g.) and zinc dust (3g./g. of steroid) added with stirring. After 45 minutes the reaction mixture was diluted with chloroform and neutralised with aqueous 10% sodium carbonate. The product, obtained after washing and drying the chloroform extract, was purified by preparative t.l.c. to afford the pure title compounds.

NOTES TO TABLE II

1. Crude product.
2. Unpurified ester as obtained from the previous stage.
3. Yields of pure product.

4. Yield with respect to 3α-nitro-oxy-5α-androstan-11-one, 17β-carboxylic acid.

and ether. The ethereal solution was washed with water, dried, and evaporated to give a residue (1.61g.)

TABLE II.

Preparation of 3α-hydroxy-17β-morpholino alkoxycarbonyl-5α-androstan-11-ones.

| Start. Material mmole. | Stage 1 R₁ | Product Yd.%[3] | [α]_D | C.% | Start. Material mmole. | Stage 2 R₂ | Product Yd.%[3] | [α]_D | C.% |
|---|---|---|---|---|---|---|---|---|---|
| 5.3 | —(CH₂)₃Cl | 85 | +61 | 0.9 | 2.2 | —(CH₂)₃N⏋O | 82 | +49 | 1.0 |
| 5.3 | —(CH₂)₄Cl | 42 | +54.5 | 0.6 | 2.1 | —(CH₂)₄N⏋O | 40 | +42 | 0.4 |
| 5.3 | —(CH₂)₅Cl | ca.90[1] | +61.5 | 0.5 | cal.7[2] | —(CH₂)₅N⏋O | 47[4] | +47 | 1.0 |
| 3.8 | —(CH₂)₆Cl | 65 | +58 | 0.5 | ca2.8[2] | —(CH₂)₆N⏋O | 45[4] | +47 | 1.0 |
| 5.4 | —CH(CH₂Cl)(CH₂Cl) | 68 | +57 | 0.9 | 0.98 | —CH(CH₂N⏋O)(CH₂N⏋O) | 15 | +57 | 1.0 |

EXAMPLE 22

2β-Ethoxy-3α-hydroxy-17β-(2-morpholinoethoxycarbonyl)-5α-androstan-11-one

A solution of 2β-ethoxy-3α-nitrato-5α-androstan 11-one 17β-carboxylic acid (510 mg.,) and oxalyl chloride (1.0 ml.) in dry benzene (25 ml.) was refluxed for 2.5 hr. and then evaporated to dryness. The residual 17β-chlorocarbonyl-2β-ethoxy-3α-nitrato 5α-androstan-11-one (ca. 510 mg.) was dissolved in ether (15 ml.) and morpholino ethanol (1 ml.) added. After standing for 18 hr. the reaction mixture was diluted with ether, filtered, washed with water and dried. Filtration and evaporation afforded 2β-ethoxy-17β-(2-morpholinoethoxycarbonyl)-3α-nitrato-5α-androstan-11-one (573 mg.) as an oil. This crude product (510 mg.) was dissolved in glacial acetic acid (10 ml.) and zinc dust (1.5 g.) added. After 1 hr. the reaction mixture was filtered, the solids being washed with chloroform. The filtrate was washed with water, aqueous 10% sodium bicarbonate, and water before being dried. Filtration and evaporation afforded a white foam which was purified by preparative t.l.c. to give the title compound (332 mg.); [α]_D + 50°.

EXAMPLE 23

17β-ethoxycarbonylmethoxycarbonyl-3α-hydroxy-5α-androstan-11-one

Triethylamine (4.5 mmole) was added to a solution of 3α-hydroxy-5α-androstan-11-one 17β-carboxylic acid (1.025g.,) in warm acetone (50 ml.) followed by ethyl bromoacetate (6 mmole) and the reaction mixture stood at room temperature overnight. The reaction was completed by refluxing for 1 hr., evaporating to dryness and partitioning the residue between water which was purified by preparative t.l.c. to afford the pure title compound; [α]_D + 76°.

EXAMPLE 24

17β-Cyanomethoxycarbonyl-3α-hydroxy-5α-androstan-11-one

Triethylamine (4.5 mmole) was added to a solution of 3α-hydroxy-5α-androstan-11-one 17β-carboxylic acid (1.025g.) in warm acetone (50 ml.) followed by chloroacetonitrile (6 mmole). After refluxing this mixture for 3 hr. further chloroacetonitrile (6 mmole) was added and refluxing continued for 4 hr. Removal of the solvent afforded a residue which was partitioned between ether and water. The ethereal solution was washed with water, dried (MgSO₄) and evaporated, to give a foam (1.187g.) which was purified by preparative t.l.c. to afford the pure title compound; m.p. 142°–146°; [α]_D + 74°.

EXAMPLE 25

3α-Hydroxy-17β-methoxycarbonyl-16α-methyl-5α-androstan-11-one

A solution of 3α-hydroxy-16α-methyl-5α-androstan-11-one 17β-carboxylic acid (1.og.) in dry 4% methanolic hydrogen chloride (20 ml.) was refluxed for 3 hrs., cooled and poured into water (200 ml.). After neutralisation the mixture was stirred (30 min.) and filtered to give a solid which, after passing through a small column of florisil and crystallisation from methylene chloride/cyclohexane, gave the title compound (580 mg.); m.p. 173°–174°; [α]_D + 76.3°,

EXAMPLE 26

2β-Ethoxy-3α-hydroxy-17β-(2'-morpholinoethoxycarbonyl)-5α-androstan-11-one salts (Dihydrogen citrate, hydrochloride, mesylate, dihydrogen phosphate)

Aqueous $_{10}$ M citric acid (hydrochloric acid, methane sulphonic acid, phosphoric acid) (1 equivalent) was added to a solution of 2β-ethoxy-3α-hydroxy-17β(2-morpholinoethoxycarbonyl)-5-androstan-11-one in ethanol. This solution was evaporated to dryness, water added and the mixture filtered. The filtrate was diluted with water to give solutions of the title compounds at a concentration of 10 mg./ml. with respect to steroid free base taking into account the material removed by filtration.

EXAMPLE 27

2β-Bromo-17β-cyano-3α-hydroxy-5α-androstan-11-one

Aqueous 48% hydrobromic acid (60 ml.) was added to a solution of 17β-cyano-2α,3α-epoxy-5α-androstan-11-one (3.03g.) in chloroform (175ml.) and the mixture stirred at room temperature for 1 hr. The organic phase was separated, washed with aqueous 10% sodium bicarbonate and water and dried. Filtration and evaporation followed by preparative t.l.c. afforded the pure title compound as a white froth (2.16g.); $[\alpha]_D + 68.5°$, (c 0.6).

EXAMPLE 28

17β-Cyano-3α-hydroxy-5α-androst-1-en-11-one.

A solution of 2β-bromo-17β-cyano-3α-hydroxy-5α-androstan-11-one (3.0g.[60% pure]), dihydropyran (7.5 ml.) and p-toluenesulphonic acid (60 mg.) in benzene (150 ml.) was stirred at room temperature for 15 minutes. The reaction mixture was washed with aqueous 10% sodium bicarbonate and water prior to being dried and evaporated to afford the tetrahydropyranyl ether as a gum. The gum was dissolved in dry dimethylacetamide (75 ml.) to which was added anhydrous lithium bromide (13.5g.) and calcium carbonate (10g.). This mixture was heated (100°) for 6 hr. followed by cooling, dilution with chloroform and filtration. The chloroform solution was washed with water, dried, filtered and evaporated. The residue was dissolved in methanol containing aqueous 2N-hydrochloric acid (1 ml.). After 4 hr. at room temperature the methanol was removed by evaporation and chloroform added. This solution, after being washed with aqueous 10% sodium bicarbonate and water, was dried, filtered and evaporated to a gum which, after preparative t.l.c. and crystallisation from chloroform/petrol, yielded the pure title compound as white needles (418 mg); m.p. 168°–175°; $[\alpha]_D + 31.5°$.

EXAMPLE 29

3α-Hydroxy-17β-methoxycarbonyl-3β-methyl-5α-androstan-11-one

Bromine (0.54 ml.) was added to a solution of sodium hydroxide (1.5 g.) in water (13 ml.) at −5° over a period of 5min. Cold dioxan (9 ml.) was then added and the resulting solution was added to a solution of 3α-hydroxy-3β-methyl-5α-pregnane-11,20-dione (1.0 g.) in dioxan (40 ml.) at 0°. The resulting mixture was kept at 5° for 1 hr., neutralised with concentrated hydrochloric acid and poured into water. Excess 2N-hydrochloric acid was then added and the precipitated solid was collected by filtration, dried in vacuo and dissolved in tetrahydrofutan (100 ml.). The resulting solution was treated with excess ethereal diazomethane at room temperature for 15 min. A few drops of acetic acid were then added and the mixture was partitioned between water and ether. The organic layer was washed with water, dried (MgSO$_4$) and evaporated. Recrystallisation of the residue gave the title compound (0.49 g., 45%) as white needles, m.p. 150°; $[\alpha]_D + 77°$ (c 1.0). (Found: C, 72.4; H, 9.2. C$_{23}$H$_{34}$O$_4$ Inquires C, 72.7; H, 9.4%)

EXAMPLE 30

3α-Hydroxy-17β-methoxycarbonyl-5α-androst-1-en-11-one

A solution of 2β-bromo-3α-hydroxy-17β-methoxycarbonyl-5α-androstan-11-one. (3.48g.,), dihydropyran (8 ml.) and p-toluenesulphonic acid (60 mg.) in benzene (150 ml.) was stirred at room temperature for 15 minutes before being washed with aqueous 10% sodium bicarbonate and water. The benzene solution was dried and evaporated to give a gum which was dissolved in dimethylacetamide (120 ml.). After the addition of anhydrous lithium bromide (14.4g.) and calcium carbonate (11.2g.) the mixture was heated (100°) for 6 hr. Cooling, dilution with chloroform and filtration gave a solution which was washed with water, dried, filtered and evaporated. The residue was dissolved in methanol (200 ml.) containing aqueous 2N hydrochloric acid (1 ml.) After 4 hr. the methanol was removed by evaporation and chloroform added. This solution, after being washed with aqueous 10% sodium bicarbonate and water, was dried, filtered and evaporated to an oil. The addition of ether resulted in crystallisation of the title compound (1.125g.); m.p. 172°–175°; $[\alpha]_D + 40°$, (c 0.7).

EXAMPLE 31

3α-Hydroxy-17β-(3'-morpholinopropoxycarbonyl)-5α-androstan-11-one

A solution of 17β(3'-morpholinopropoxycarbonyl)-5α-androstan-3,11-dione (140 mg.) in isopropanol (1 ml.) was added to a "stock" solution of the chloroiridic acid reagent (7 ml.) which had been neutralised to ca. pH 6 with triethylamine immediately prior to the addition. After refluxing for 7 hr., isolation of the product afforded a gum (150 mg.) which, after purification by preparative t.l.c., gave the title compound as a white froth; 112 mg., $[\alpha]_D + 51°$ (c, 0.6,).

EXAMPLE 32

(a) 11α-Hydroxy-19-norpregna-4,16-diene-3,20-dione

-A solution of 11α,17α-dihydroxy-19-norpregn-4-ene-3,20-dione (4 g.,) and semicarbazide hydrochloride (4 g.) in methanol (200 ml.) was refluxed for 2 hr. The methanol was then removed by distillation under reduced pressure and water was added to the residue. The precipitated solid was collected by filtration, washed with water and dried over P$_2$O$_5$ in vacuo.

A solution of this solid in a mixture of glacial acetic acid (80 ml.), water (28 ml.) and pyruvic acid (4 ml.) was heated on a steam bath for 1 hr. The resulting solution was concentrated under reduced pressure and partitioned between saturated aqueous sodium bicarbonate and ethyl acetate The organic layer was washed with water, dried (Na₂SO₄) and evaporated to dryness. The residue was subjected to preparative t.l.c.(CHCl₃, (CH₃)₂CO: 15 : 1,) and crystallised from acetone/petrol to afford title compound (1.6 g.) as white needles, m,p. 149°.

(b) 19-nor-5α-pregna-3,11,20-trione

A solution of 11α-hydroxy-19-norpregna-4,16-diene-3,20-dione in dry tetrahydrofuran (200 ml.) was added over 5 mins. to a solution of lithium (5 g.) in liquid ammonia (2.5 litres). The solution was then left for 30min. Ethanol (ca. 100ml.) was then added until the blue colour had been discharged and the ammonia was then allowed to evaporate. The residue was partitioned between water and ether. The organic layer was washed, dried (Na₂SO₄) and evaporated to give crude 3ε,11α,20ε-trihydroxy-19-nor-5α-pregnane (1.5 g.)

A solution of this in acetone (40 ml.) was treated dropwise with Jones reagent (5 ml) [a solution of chromium trioxide (267 g.) in a mixture of concentrated sulphuric acid (230 ml.) and water (400 ml.) made up to 1 liter with water (8N w.r.t. oxygen)], at room temperature. The resulting solution was partitioned between water and ethyl acetate. The organic layer was washed with water, dried (Na₂SO₄) and evaporated. The residue was subjected to preparative t.l.c. (CHCl₃) and recrystallised from acetone/petrol to afford title compound (0.44 g.)

(c) 3α-Hydroxy-19-nor-5α-pregnane-11,20-dione

A solution of 19-nor-5α-pregnane-3,11,20-trione (0.9 g., 0.28 mmole)) in "stock" chloroiridic solution (75 ml.) was refluxed for 24 hr. The solution was then cooled, partitioned between water and ether and the organic layer was washed well with water, dried (Na₂SO₄) and evaporated. The residue was subjected to preparative t.l.c. (EtOH) and recrystallised from acetone to afford title compound (0.6 g;) as white needles, m.p. 154°, $[\alpha]_D$ + 200°.

3α-Hydroxy-17β-methoxycarbonyl-19-nor-5α-androstan-11-one

Bromine (5.25 ml.) was added to a stirred solution of sodium hydroxide (14.7 g.) in water (110 ml.) at −5° at such a rate so as to maintain the temperature between −5° and 0°. Cooled dioxan (85 ml.) was added and the mixture kept at 0°. A portion (9 ml.) of this solution was added to a solution of 3α-hydroxy-19-nor-5α-pregnane-11,20-dione (0.4 g.) in dioxan (15 ml.) and water (4 ml.) at 8° and the resulting mixture was stirred for 3 hr. between 5° and 10°. A solution of sodium sulphite (250 mg.) in water (1 ml.) was added and the mixture was refluxed for 15 min. The hot solution was acidified with hydrochloric acid to pH 3, filtered hot and evaporated until crystallisation had begun. Water (80 ml.) was added with stirring and the resulting precipitate was collected by filtration, washed and dried over P₂O₅ in vacuo.

A solution of this solid (174 mg.) in methanol (5 ml.) and ether (5 ml.) was treated at 0° with an excess of dry ethereal diazomethane prepared by adding N-nitrosomethylurea (5 g.) to a stirred mixture of ether (50 ml.) and 50% w/v aqueous potassium hydroxide (15 ml.) at 5°. The ether layer was decanted and dried over potassium hydroxide pellets. The solution was left at 0° for 5 minutes, and then a drop of acetic acid was added. The resulting solution was diluted with ether (100 ml.) washed successively with saturated aqueous sodium bicarbonate and water, dried (Na₂SO₄) and evaporated. The residue was recrystallised from acetone/petrol to afford title compound (115 mg.) as white needles, m.p. 145°; $[\alpha]_D$ + 140 (c 0.8);

EXAMPLE 33

3α-Hydroxy-17β-(2'-morpholinoethoxycarbonyl)-5β-andro stan-11-one

A solution of 3α-nitro-oxy-17β-(2'-morpholinoethoxycarbonyl)-5β-androstan-11-one (606 mg.) in glacial acetic acid (15 ml.) was stirred for 1 hour with zinc powder (1.25 g.). The zinc was removed by filtration, washed with chloroform (300 ml.). The combined filtrates were washed with water, saturated sodium bicarbonate solution, water, dried (Na₂SO₄) and evaporated to a white foam (553 mg.). Purification of this foam by preparative t.l.c. (CHCl₃) yielded title compound, 384 mg. as an offwhite foam; $[\alpha]_D$ + 54° (c 1.066).

EXAMPLE 34

3α-Hydroxy-17β(2'-morpholinoetnoxycarbonyl)-5β-androstane

Zinc dust (4.0 g.) was added to a stirred solution of 3α-nitro-oxy-17β(2'-morpholinoethoxycarbonyl)-5β-androstane (2.33 g.) in glacial acetic acid (40 ml.). After 20 minutes the reaction mixture was diluted with chloroform (100 ml.) and neutralised with aqueous sodium carbonate (10%). After filtration and separation the organic phase was washed with water, dried (MgSO₄), filtered and evaporated to give a white froth (2.29 g.). A sample (490 mg.) was purified by preparative t.l.c. (ethanol/chloroform 1:19), to give a froth which was rechromatographed (ethanol/acetone 1:49) to give title compound (222 mg.) as a white froth; $[\alpha]_D$ + 35°, (c 0.75%).

EXAMPLE 35

3α-Hydroxy-17β(2'-morpholinoethoxycarbonyl)-5α-androstane

A solution of 17β(2'-morpholinoethoxycarbonyl)-5α-androstan-3-one (750 mg.) in the minimum volume of isopropanol was added to a stock solution (35 ml.) of chloroiridic acid/trimethyl phosphite complex preneutralised to pH5 with triethylamine (3 ml.). This solution, after being refluxed for 4.5 hours, was poured into water and extracted with chloroform. The chloroform solution was washed with water, dried (MgSO₄) and filtered through a short column of florisil before evaporation to a gum (740 mg.). Purification by preparative t.l.c. (ethanol/chloroform 1:19) afforded title compound (545 mg.) as a white froth; $[\alpha]_D$ + 37.8, (c 0.9%).

EXAMPLE 36

17β-Cyano-3α-hydroxy-5β-androstan-11-one

Zinc dust (1.0 g.) was added to a solution of 17β-cyano-3α-nitro-oxy-5β-androstan-11-one (500 mg.) dissolved in glacial acetic acid (7.5 ml.) and tetrahydrofuran (5 ml.). After stirring at room temperature for 15 minutes the reaction mixture was diluted with chloroform (50 ml.) and neutralised (ca. pH6) with aqueous sodium carbonate (10%). The organic phase was separated, filtered, washed with water and dried (MgSO₄). The chloroform solution was evaporated to give title compound (500 mg.) as a white froth.

An analytical sample was obtained by preparative t.l.c. (ethanol/chloroform 1:49): m.p. 190°–2°; $[\alpha]_d$: 78°, (c 0.6%).

EXAMPLE 37

17β-Cyano-3α-hydroxy-5β-androstane

Zinc dust (1.0 g.) was added to a solution of 17β-cyano-3α-nitro-oxy-5β-androstane (750 mg.) dissolved in glacial acetic acid (10 ml.) and stirred at room temperature for 15 minutes. The reaction mixture was diluted with chloroform (50 ml.), filtered and washed with water, aqueous sodium bicarbonate and water. Drying (MgSO₄), filtration and evaporation afforded a crystalline solid (674 mg.). Recrystallisation (x 2) from chloroform/petrol afforded title compound as white needles; m.p. 156.5–158.5°; $[\alpha]_D + 77°$, (c 1.3%).

EXAMPLE 38

17β-Cyano-3α-hydroxy-5α-androstane

A solution of 17β-cyano-5α-androstan-3-one (1.0 g.) in the minimum volume of isopropanol (ca. 75 ml.) was added to a stock solution of chloroiridic acid/trimethyl phosphite complex (50 ml.) preneutralised to pH4 with triethylamine (4 ml.). This solution, after being refluxed for 20 hours, was poured into water (200 ml.) and extracted with chloroform. The chloroform solution was washed with water, dried (MgSO₄), filtered and evaporated to a gum (1.13 g.). This was subjected to preparative t.l.c. eluting successively with ethanol/chloroform (1:49) and ethyl acetate/benzene (1:19). The main band was removed between the eluant change and the final elution was repeated four times before removing the main band. This gave pure title compound (195 mg.) as a white solid; m.p. 156°–159°; $[\alpha]_D + 56°$ (c 0.4%).

EXAMPLE 39

17β-Cyano-3α-hydroxy-5α-androst-1-ene p-Toluenesulphonic acid (10 mg.) was added to a stirred solution of 2β-bromo-17β-cyano-3α-hydroxy-5α-androstane (2.65 g.,) and dihydropyran (10 ml.) in dry benzene (200 ml.). After 45 minutes at room temperature the solution was washed with aqueous 10% sodium bicarbonate (25 ml.) and water prior to being dried (MgSO₄), filtered and evaporated to give crude 2β-bromo-17β-cyano-3α-(tetrahydropyran-2'ξ-yloxy)-5α-androstane. A mixture of calcium carbonate (15 g.), anhydrous lithium bromide (22.5 g.) and the tetrahydropyranyl derivative in dimethylacetamide (100 ml.) was stirred and heated on an oil bath (110°) for 6 hours. After cooling, the reaction mixture was diluted with chloroform and washed with water before drying (MgSO₄) filtration and evaporation to a residue which was dissolved in methanol (100 ml.) and aqueous 2N hydrochloric acid (2 ml.). After 2½ hours at room temperature and methanol was removed by evaporation and the residue dissolved in chloroform (25 ml.). This solution was washed with aqueous 10% sodium bicarbonate (25 ml.) and water (25 ml.) before drying (MgSO₄), filtration and evaporation to a gum (2.55 g.). A sample (1.0 g.), after preparative TLC eluting with acetone/petrol (1:2,), afforded title compound (230 mg.,) as a white froth; $[\alpha]_D 0°$, (c 0.3). A sample was recrystallised from ether/petrol (x2); m.p. 129°–133°; $[\alpha]_P 4°$, c 0.5.

EXAMPLE 40

3α-Hydroxy-17β-(2'-morpholinoethoxycarbonyl)-5β-androstan-11-one-citrate

A solution of 3α-hydroxy-17β-(2'-morpholinoethoxycarbonyl)-5β-androstan-11-one (112 mg., 0.25 mmole) in ethanol (2 ml.) was treated with 0.01 N aqueous citric acid (2.5 ml; 0.25 mmole) and the resulting mixture was evaporated to dryness. The residue was treated with water (1.1 ml) to give an aqueous solution of the title compound (10% with respect to free steroidal base).

This solution was diluted further and clarified until the total volume was 11.2 ml. therby giving an aqueous solution (pH 3.5) of the title compound (10 mg.ml⁻¹. with respect to steroid).

EXAMPLE 41

3α-Hydroxy-2β-methyl-17β-(2'-morpholinoethoxycarbonyl)-5α-androstan-11-one

2β-Methyl-3α-nitro-oxy-11-oxo-5α-androstane-17β-carboxylic acid (1.17g.) and oxalyl chloride (3 ml.) in dry benzene (150 ml.) were refluxed gently for 3 hours, and the solution was then evaporated to a white foam (1.2 g.) which was dissolved in dry ether (100 ml.), dry dichloromethane (12 ml.) and morpholinoethanol (8.25 ml.). The solution was stirred at room temperature for 60 hours, and it was then washed (NaHCO₃ solution and H₂O), dried and evaporated to a residue (1.2g.) which was purified by preparative t.l.c. (CHCL₃ with 2% ETOH) to give 2β-methyl-17β-(2'-morpholinoethoxycarbonyl)-3α-nitro-oxy-5α-androstan-11-one (64-mg.) as a white foam.

A solution of this in glacial acetic acid (10 ml.) was treated with zinc dust (750 mg.), and the cooled (15°C) mixture was stirred for 1½hr. Chloroform (50 ml.) was added and the filtered solution was washed (H₂O, NaHCO₃ solution, and H₂O again), dried and evaporated to a foam (570 mg.) which was purified by preparative t.l.c. (CHCL₃ with 3% ETOH) to give the title compound (150 mg.) as a white foam, $[\alpha]_D 71°$.

EXAMPLE A 0.065 g. of 17β-ethoxycarbonyl-3α-hydroxy-5α-androstan-11-one were dissolved in 2 g. of Tween 80. The system was mechanically agitated at 70° in a stream of N₂ until the steroid was dissolved. The resulting solution was diluted with sterile distilled water containing 0.025 g. of sodium chloride to give a final volume of 10 ml.

EXAMPLE B 0.05 g. of 17β-cyano-3α-hydroxy-5β-androstan-11-one were dissolved in 2ml. of acetone at 20°C. The resulting solution was added to 2g of Cremophor EL at 20°C and stirred until homogeneous. The acetone was removed in a vigorous stream of nitrogen. The solution was diluted with sterile distilled water containing 0.05g of sodium chloride to give a final volume of 10ml.

The following preparations illustrate the production of some of the starting materials used in the Examples.

Preparation 1

17β-Methoxycarbonyl-3β-toluene-p-sulphonyloxy-5α-androstan-11-one

3β-Hydroxy-17β-methoxycarbonyl-5α-androstan-11-one (4.75 g.) and toluene-p-sulphonyl chloride (5 g.) in pyridine (50 ml.) were allowed to stand at room temperature for four days. Water (10 ml.) was added, the resulting solution was stirred for an hour and was then poured into stirred water (1.1). The mixture was acidified with hydrochloric acid and the product collected, washed well with water and dried over sodium hydroxide in vacuo. Recrystallisation from chloroform/hexane containing a trace of ether afforded pure title compound (3.4 g.) as needles; m.p. 158°–160°; $[\alpha]_D$ + 42.5°, (c 1.09).

Preparation 2

17β-Methoxycarbonyl-5α-androstan-2-en-11-one

A solution of 17β-methoxycarbonyl-3β-toluene-p-sulphonyloxy-5α-androstan-11-one (1.01g.) in hot collidine (5 ml.) was refluxed for 30 minutes. The solution was cooled and poured into diluted hydrochloric acid and ice, and stirred. The product was filtered, washed with water, dried and purified by filtering it through a column of alumina, eluting with ether. The eluate was evaporated to a residue and crystallisation from ether and hexane gave title compound (340 mg.) as colourless rods; m.p. 169°–175°; $[\alpha]_D$ + 139°.

Preparation 3

2α,3α-Epoxy-17β-methoxycarbonyl-5α-androstan-11-one

17β-Methoxycarbonyl-5α-androst-2-en-11-one (6.63 g.) and m-chloroperbenzoic acid (4.84 g.) were stirred with chloroform (115 ml.) for 16 hours. The solution was diluted with chloroform, washed with 2% aqueous potassium hydrogen carbonate, dried (MgSO$_4$) and evaporated to a gum. Crystallisation from ethyl acetate/light petroleum afforded pure title compound. (1.64 g.) as colourless rods; m.p. 140°–145°; $[\alpha]_D$ + 74.2°.

Preparation 4

3α,20β,21-Trihydroxy-5α-pregnan-11-one

3α,21-Dihydroxy-5α-pregnane-11,20-dione (1 g.) in ethanol (50 ml.) was stirred for 20 minutes with sodium borohydride (110 mg.) in water (5 ml.). A little glacial acetic acid was added and the solution was evaporated to small volume, poured into water and extracted with chloroform. The extract was washed with water, dried and evaporated to a foam, which was crystallised from methyl acetate to give title compound (633 mg.) as colourless needles; m.p. 222°–223°; $[\alpha]_D$ + 36°.

Preparation 5

17β-Chlorocarbonyl-3α-nitro-oxy-5α-androstan-11-one

3α-Nitro-oxy-11-oxo-5α-androstane-17β-carboxylic acid (500 mg.) and oxalyl chloride (2 ml.) were refluxed with dry benzene (50 ml.). After 5 hours the solvents were removed under reduced pressure and the resultant froth was triturated with dry ether (70 ml.). The solution was filtered, evaporated and dried in vacuo to give title compound (353 mg.) $\nu_{max}$. 1780, 1705 and 1620 cm$^{-1}$ in bromoform.

Preparation 6

3α-Nitro-oxy-11-oxo-5α-androstane-17β-carboxylic acid

Fuming nitric acid (13 ml.) was added slowly with stirring to acetic anhydride (40 ml.) between —5° and 0°. This nitrating mixture was stirred with a solution of 3α-hydroxy-11-oxo-5α-androstane-17β-carboxylic acid (8 g.) in chloroform (240 ml.) for 1 hour, between —5° and 0°. The mixture was poured into 2N-sodium hydroxide solution and stirred for 30 minutes. The mixture was extracted with chloroform and the combined extracts were washed with water and evaporated to a residue. The residue was stirred for 1 hour with ethanol (50 ml.), ether (250 ml.) and water (500 ml.), the pH being adjusted to 10–11 with sodium hydroxide. The aqueous layer was acidified with hydrochloric acid and extracted with chloroform. The extract was washed with water, dried (Na$_2$SO$_4$) and evaporated to a residue. Crystallisation from chloroform and benzene gave title compound (4.707 g.) as colourless rods, m.p. 214°–218° (dec.), $[\alpha]_D$ + 73°.

Preparation 7

3α-Hydroxy-11-oxo-5α-androstane-17β-carboxylic acid

A solution of sodium hydroxide (2.1 g.) in water (18 ml.) was stirred at —5° and bromine (0.75 ml.) was added slowly, the temperature being maintained between —5° and 0°. Cold dioxan (12 ml.) was added. This sodium hypobromite solution was stirred at 0° until required.

3α-Hydroxy-5α-pregnane-11,20-dione (1.4 g.) was dissolved in dioxan (55 ml.) and water (16 ml.) and stirred at 5°. The sodium hypobromite solution was added and the mixture stirred for 3 hours between 5° and 10°.

Sodium sulphite heptahydrate (800 mg.) in water (5 ml.) was added and the mixture refluxed for 15 minutes.

The mixture was acidified while hot with concentrated hydrochloric acid, filtered, evaporated until crystals appeared and extracted into chloroform. The extract was washed with water, dried and evaporated to a residue which was crystallised from benzene, chloroform and petrol to give title compound (660 mg.) as colourless needles; m.p. 265°–270°, Preparation 8

5α-Androst-2-en-11-one-17β-carboxylic acid

A solution of 17β-methoxycarbonyl-5α-androst-2-en-11-one (4.6g.,) in 3% ethanolic potassium hydroxide (50 ml.) was refluxed under N$_2$ for 36 hr. and then concentrated to small volume prior to pouring into water. After acidification the solid product was filtered, dried and recrystallised from chloroform/benzene to give the title compound (2.53 g.), m.p. 201°–214°; $[\alpha]_D$ + 129°

Preparation 9

2α,3α-epoxy-5α-androstan-11-one-17β-carboxylic acid.

A solution of 5α-androst-2-en-11one 17β-carboxylic acid (1.397 g.) and m-chloroperbenzoic acid (850 mg.) in chloroform (20 ml.) was stirred at room temperature for 3.25 hr. and then diluted with chloroform (75 ml.) prior to washing with 10% aqueous sodium bicarbonate and water. The chloroform solution was dried, filtered and evaporated to give a foam (1.04g.) which, after preparative t.l.c. afforded the pure title compound as a foam; $[\alpha]_D$ + 69°, (c 0.3).

Preparation 10

2β-Ethoxy-3α-hydroxy-5α-androstan-11-one-17β-carboxylic acid

A solution of 2α,3α-epoxy-5α-androstan-11-one-17β-carboxylic acid (940 mg.) and concentrated sulphuric acid (0.25 ml.) in dry ethanol (30 ml.) was stirred at room temperature for 30 minutes. Water (100 ml.) was added and the reaction mixture extracted with chloroform. The chloroform solution was washed with water, dried, filtered and evaporated to give a froth which solidified when triturated with chloroform/petrol. Filtration afforded the solid crude product (752 mg.) which, after recrystallisation from ethanol/water, afforded the pure title compound; m.p. 249°–260°; $[\alpha]_D + 74°$, (c 0.33).

Preparation 11

2β-Ethoxy-3α-nitro-oxy-5α-androstan-11-one 17β-carboxylic acid

Fuming nitric acid (1.3 ml.) was added dropwise to acetic anhydride (4 ml.) keeping the temperature of the reaction mixture between −5° and 0°. A solution of 2β-ethoxy-3α-hydroxy-5α-androstan-11-one 17β-carboxylic acid (806 mg.) in chloroform (30 ml.) was added to the nitrating agent keeping the temperature between −5° and 0° for ca. 1 hr. The reaction mixture was poured into aqueous 2N sodium hydroxide (29 ml.) and, after stirring for 20 min., separated, the aqueous phase being further extracted with chloroform. The residue, after evaporation of the chloroform was dissolved in ether (25 ml.), ethanol (5 ml.) and water (50 ml.) before being made alkaline. The aqueous phase was separated, acidified and extracted with chloroform. The extract afforded, after being washed, dried, filtered and evaporated, the title compound as a white foam (570 mg.); $[\alpha]_D + 77°$,

Preparation 12

3α-Hydroxy-16α-methyl-5α-androstan-11-one 17β-carboxylic acid.

A solution of sodium hydroxide (7.35g.) in water, (55 ml.) was stirred at −5° and bromine added slowly maintaining the temperature between −5° and 0°. Cold dioxan (45 ml.) was added and the pale yellow sodium hypobromite solution stirred at 0° until required. 3α-Hydroxy-16α-methyl-5α-pregnane-11, 20-dione (5.0g.) was dissolved in dioxan (200 ml.) and water (55 ml.). The hypobromite solution was added over 5 min. and the resulting mixture kept between 5° and 10° with stirring for 3 hr. Sodium sulphite heptahydrate (2.8g.) in water (15 ml.) was added and the solution refluxed for 15 min. The mixture was acidified and concentrated to incipient crystallisation before pouring into water (1 l.). Filtration afforded the title compound (3.85g.); m.p. 265°–268°.

Preparation 13

17β-Carbamoyl-5α-androst-2-en-11-one

A solution of 5α-androst-2-en-11-one 17β-carboxylic acid (6.3g.) in dry benzene (200 ml.) and oxalyl chloride (15.75 ml.) was refluxed for 1.5 hr. The mixture was evaporated to give 17β-chlorocarbonyl-5α-androst-2-en-11-one as a gum which shaken with 880 ammonia (100 ml.), benzene (32 ml.) and water (32 ml.) After 1 hr. the mixture was extracted with ether.

The ethereal solution was washed ($H_2O$), dried and evaporated to give a froth. Crystallisation from chloroform/petrol afforded the title compound (1.9g.); m.p. 92°–96°; $[\alpha]_D + 95.5°$, (c 0.75).

Preparation 14

17β-Cyano-5α-androst-2-en-11-one

17β-Carbamoyl-5α-androst-2-en-11-one (4.0g., 13 mmole) and polyphosphate ester (20g.) were refluxed in chloroform (200 ml.) for 20 hr. The chloroform was removed by evaporation and the residue stirred with aqueous 10% sodium carbonate (150 ml.) for an hour. The mixture was extracted with ether and the extract washed ($H_2O$), dried filtered and evaporated to give a solid which, after recrystallisation from chloroform/cyclohexane, gave the title compound (2.17g); m.p. 189°–191°; $[\alpha]_D + 152°$, (c 0.9).

Preparation 15

17β-Cyano-2α,3α-epoxy-5α-androstan-11-one

A solution of 17β-cyano-5α-androst-2-en-11-one (2.8g.) and 85% m-chloroperbenzoic acid (2.0g.) in chloroform (50 ml.) was stirred for 1.5 hour at room temperature and then diluted with chloroform (75 ml.). This solution was washed with aqueous 10% sodium bicarbonate and water prior to drying. Filtration and evaporation afforded a solid (3.18g.) which was recrystallised from ether/petrol to afford the pure title compound; m.p. 206°–208°; $[\alpha]_D + 93°$, (c 0.7).

Preparation 16

3α-Hydroxy-16α-methyl-5α-pregnane-11,20-dione

To a stirred slurry of cuprous iodide (950 mg) in dry ether (75 ml) under dry nitrogen at 0° was added a solution of methyl-lithium in ether (1.6M; 6 ml.) until the initially formed yellow precipitate just redissolved to give a clear solution. To the stirred solution at 0° was added a solution of 3α-hydroxy-5α-pregn-16-ene-11,20-dione (600 mg) in dry tetrahydrofuran (50 ml.). During the addition a bright yellow precipitate formed. The mixture was stirred at 0° for 30 minutes, and then poured into cold, saturated ammonium chloride solution (200 ml.) More ether (200 ml) was added and the organic layer was separated, washed with saturated ammonium chloride solution (200 ml) and with water (200 ml.) dried over sodium sulphate and purified by preparative t.l.c. in ethyl acetate to give a product which was further purified by preparative t.l.c. in ethyl acetate/chloroform, 1/1 to give a white solid (380 mg) which was recrystallised from ether/petrol to give title compound (248 mg) as colourless plates, m.p. 138°–140°, $[\alpha]_D + 99°$, (c 0.95).

Preparation 17

2'-N,(N-ethyl, p-methoxyanilino) ethanol.

N-Ethyl anisidine hydrochloride (15g.) was dissolved in aqueous 2N sodium hydroxide (65 ml.) and the free base extracted with ether. After removal of the ether the amine was heated to ca 120° while ethylene chlorohydrin was added over 15 min. The reaction mixture was heated for a further 45 min. cooled and stood at room temperature overnight before being poured into aqueous 5N sodium hydroxide. Extraction with benzene followed by distillation at reduced pressure afforded the title compound (7.7g.); b.p. 135°–140°/0.2 mm;

Preparation 18

17β(3′-Morpholinopropoxycarbonyl)-5α-androstane-3,11-dione

Jones reagent (0.4 ml.) was added to a solution of 3α-hydroxy-17β(3′-morpholinopropoxycarbonyl)-5α-androstan-11-one (325 mg.) in acetone (5 ml.). After stirring (20 min.) the reaction mixture was diluted with chloroform and washed with aqueous 10% sodium bicarbonate and water. The chloroform solution was dried, filtered and evaporated to give a gum (238 mg.) which, after purification by preparative thick layer chromatography, afforded the pure title compound; $\nu_{max.}^{CHBr_3}$ 1703 (-C=O) and 1720 cm$^{-1}$ (-COOR), (-OH absent).

Preparation 19

(a)
(3R)-20-20-Ethylenedioxy-11-oxo-5α-pregnane-3-spiro-2′-oxirane

A mixture of sodium hydride (17 mg.), trimethylsulphoxonium iodide (300 mg.) and dimethyl sulphoxide (2 ml.) was stirred under nitrogen at room temperature for 1 hr. 5α-Pregnane-3,11,20-trione 20-ketal (100 mg.) was then added and the resulting mixture was stirred for a further 2 hr. and poured into water. The precipitated solid was collected by filtration, washed with water and dried over $P_2O_5$ in vacuo. Recrystallisation from acetone/petroleum ether gave the title compound (50 mg., 46%), as white needles, m.p. 176°–177°; $[\alpha]_D + 49°$.

(b)
20,20-Ethylenedioxy-3β-methyl-5α-pregnane-3α,11β-diol

A solution of (3R)-20,20-ethylenedioxy-11-oxo-5α-pregnane-3-spiro-2′-oxirane (1.0 g.) in tetrahydrofuran (5 ml.) was added to a stirred suspension of lithium aluminum hydride (0.5 g.) in ether (15 ml.). The resulting mixture was refluxed for 2 hr. treated with saturated aqueous ammonium chloride and partitioned between water and ether. The organic layer was washed with water, dried ($Na_2SO_4$) and evaporated. Recrystallisation of the residue from acetone gave the title compound (0.9 g., 90%) as white needles, m.p. 162°, $[\alpha]_D + 35°$ (Found: C, 72.8; H, 10.2. $C_{24}H_{40}O_4 \cdot \frac{1}{4} H_2O$ requires C,72.8; H, 10.3%).

(c) 3α-Hydroxy-3β-methyl-5α-pregnane-11,20-dione.

A solution of 20,20-ethylenedioxy-3β-methyl-5α-pregnane-3α,11β-diol (1.5 g) in acetone (60 ml.) was treated with a solution of potassium dichromate (1.5 g.) in 2N-sulphuric acid (15 ml.) at room temperature for 2 hr. The mixture was then poured into water and the precipitated solid was collected by filtration, washed with water and dried over phosphorus pentoxide in vacuo. Recrystallisation from acetone-petroleum ether gave the title compound (0.75 g; 60%) as white needles, m.p. 175°; $[\alpha]_D + 116°$ (Found: C, 75.7; H, 9.8. $C_{22}H_{34}O_3$ requires C, 75.5; H, 9.9%).

Preparation 20

3α-Nitro-oxy-11-oxo-5β-androstane-17β-carboxylic acid

Fuming nitric acid (10 ml.) was added slowly to stirred acetic anhydride (30 ml.) at −5°, the temperature being maintained between −10° and 0° during the addition. A solution of 3α-hydroxy-11-oxo-5β-androstane-17β-carboxylic acid (5.02 g.) in hot chloroform (750 ml.) was allowed to cool and then added slowly, with stirring, to the nitrating mixture. The mixture was stirred between −10° and 0° for one hour and then poured into stirred aqueous 2N sodium hydroxide (250 ml.), to give a resultant solution of pH4. After ½ hour, the chloroform layer was separated, and the aqueous layer extracted again with chloroform. The combined extracts were washed with water and evaporated to residue. Ethanol (50 ml.) was added, followed by 2N aqueous sodium hydroxide, water and ether, carefully, with stirring, keeping the steroid in solution, until the aqueous layer was about 500 ml. at pH 10-11, and 250 ml. of ether had been added. The aqueous layer was separated, acidified to pH4 with 2N hydrochloric acid and stirred with chloroform (300 ml.), until the aqueous layer was clear. The chloroform layer was separated, washed with water, dried ($Na_2SO_4$) and evaporated to a residue (5.33 g.). This was crystallised from chloroform and benzene to give title compound (0.97 g.) as colourless needles; m.p. 211°–213°; $[\alpha]_D + 84°$ (c 1.01, $CHCl_3$).

Preparation 21

3α-Nitro-oxy-17β-(2′-morpholinoethoxycarbonyl)-5β-androstan-11-one

A solution of 3α-nitro-oxy-11-oxo-5β-androstane 17β-carboxylic acid (1.48 g.) in dry benzene (150 ml.) was refluxed for 2 hours with oxalyl chloride (3 ml.). The solution was evaporated to a residue, which was dried by azeotroping with benzene (2 × 50 ml.), washed with ether, filtered, and the combined filtrates evaporated to a white foam (1.45 g.). A solution of this foam in dry ether (25 ml.) and dry methylene chloride (25 ml.) was treated with 2β-hydroxyethylmorpholine (8 ml.) at room temperature. After 18 hours, the solution was diluted with chloroform (300 ml.), washed with water, dried ($Na_2SO_4$) and evaporated to a pink foam. Purification by preparative t.l.c. (acetone/petrol 1:2) yielded as major component, the title compound (864 mg.) as a white foam; $[\alpha]_D + 73°$ (c 0.98, $CHCl_3$).

Preparation 22

3α-Nitro-oxy-5β-androstane-17β-carboxylic acid

Fuming nitric acid (13 ml.) was added with stirring to acetic anhydride (40 ml.) keeping the temperature between −10 and 0°. A suspension of 3α-hydroxy-5β-androstane 17β-carboxylic acid (8.0 g.) in chloroform (300 ml.) was added to the nitrating solution, keeping the reaction temperature at ca. 0°. The reaction mixture was stirred at ca. 0° for 1.5 hours and then poured into aqueous sodium hydroxide (290 ml. 2N). This, after stirring (20 minutes), was separated and the aqueous phase further extracted with chloroform (100 ml.). The residue, following evaporation, was dissolved in ethanol (50 ml.), water (500 ml.) and ether (250 ml.) and the whole solution brought to ca. pH10 with aqueous sodium hydroxide (2N). After separation, the aqueous phase was stirred and acidified with aqueous hydrochloric acid (2N) whereupon the product precipitated as a white solid. This was filtered, washed with water, and dried to afford title compound (8.5 g.) as a white solid; m.p. 221°–223°. A sample was recrystalised from chloroform/petrol; white flakes, m.p. 222°–225°dec.; $[\alpha]_D + 75°$, (c 0.4%).

Preparation 23

3α-Nitro-oxy-17β(2'-morpholinoethoxycarbonyl)-5β-androstane

A solution of oxalyl chloride (10 ml.) and 3α-nitro-oxy-5β-androstane-17β-carboxylic acid (5.4 g.) in benzene (250 ml.) was refluxed gently for 3 hours and then evaporated to dryness to afford 17β-chlorocarbonyl-3α-nitro-oxy-5β-androstane (6.0 g.) as a white waxy solid. A solution of morpholinoethanol (7 ml.) and the acid chloride (2.6 g.) in ether (200 ml.) was stirred at room temperature for 16 hours. After the addition of water (50 ml.) the reaction mixture was separated and the ethereal phase washed with water. After drying (MgSO$_4$), filtration and evaporation afforded a white froth (2.86 g.). A sample (500 mg.), after purification by preparative t.l.c. (ethanol/chloroform 1:19) afforded title compound (337 mg.) as a white froth; $[\alpha]_D$ + 67°, (c 0.76).

Preparation 24

17β-(2'-morpholinoethoxycarbonyl)-5α-androstan-3-one

A solution of 5α-androstan-3-one 17β-carboxylic acid (2.1 g., corrected for the presence of 15% 5α-pregnan-3,20-dione) and oxalyl chloride (4 ml.) in dry benzene (125 ml.) was refluxed for 1.5 hours before evaporation to dryness to afford crude 17β-chlorocarbonyl-5α-androstan-3-one. Morpholinoethanol (5 ml.) was added to a stirred solution of the acid chloride in dry ether (125 ml.) and pyridine (3 ml.) at room temperature. After 1 hour the mixture was diluted with ether (100 ml.) and washed with aqueous 10% sodium hydroxide and water, dried (MgSO$_4$), filtered and evaporated to give a gum (3.275 g.). A sample (2.0 g.) gave, after purification by preparative t.l.c. (ethanol/chloroform 1:19) title compound (900 mg.) as a white froth; $[\alpha]_D$ + 54.5°, (c. 0.9).

Preparation 25

17β-Carbamoyl-3α-nitro-oxy-5β-androstan-11-one

A solution of 3α-nitro-oxy-5β-androstan-11-one-17β-carboxylic acid (2.0 g.) and oxalyl chloride (3 ml.) in dry benzene was refluxed for 1.5 hr. and then evaporated to dryness to give 17β-chlorocarbonyl-3α-nitro-oxy-5β-androstan-11-one. A mixture of ammonia (880, 16 ml.), benzene (10 ml.) and water (10 ml.) was added to the acid chloride and the whole mixture, after being shaken vigorously for 5 minutes, stood at room temperature for 1 hour. The white precipitate was removed by filtration, washed with water and dried. The crude product (1.9 g.) was recrystallised from chloroform/cyclohexane to give title compound (1.65 g.) as white crystals; $[\alpha]_D$ + 82°, (c 0.6%); m.p. 112°–117°.

Preparation 26

17β-Cyano-3α-nitro-oxy-5β-androstan-11-one

A solution of 17β-carbamoyl-3α-nitro-oxy-5β-androstan-11-one (1.5 g.) and polyphosphate ester (7.5 g.) in chloroform (80 ml.) was refluxed for 7 hours. A further portion of polyphosphate ester was added and refluxing continued for a further 3 hours. The chloroform was removed by evaporation and, after the addition of aqueous sodium carbonate (75 ml., 10%) and standing for ca. 30 minutes, the reaction mixture was extracted with ether. The ethereal solution was washed with water, dried (MgSO$_4$) and evaporated to give a buff solid (1.47 g.). Crystallisation from chloroform/cyclohexane gave title compound (775 mg.) as white crystals: $[\alpha]_D$ 118.5°, (C 0.9%); m.p. 214°–215°.

Preparation 27

17β-Carbamoyl-3α-nitro-oxy-5β-androstane

A solution of ammonia (880, 30 ml.) and water (25 ml.) was added to a solution of 17β-chlorocarbonyl-3α-nitro-oxy-5β-androstane (3.5 g.) in benzene (25 ml.). After stirring for 1 hour followed by standing at room temperature for 16 hours the mixture was extracted with ether, dried (MgSO$_4$), and evaporated, to give a white froth (3.11 g.). A sample (500 mg.) was purified by preparative t.l.c. (ethanol/chloroform 1:19) followed by crystallisation from ether/petrol to give title compound (361 mg.) as a white amorphous solid; softened and decomp. >75°; $[\alpha]_D$ + 61°, (c 0.35%).

Preparation 28

17β-Cyano-3α-nitro-oxy-5β-androstane

A solution of 17β-carbamoyl-3α-nitro-oxy-5β-androstane (2.54 g.) and polyphosphate ester (15 g.) in chloroform (100 ml.) was refluxed for 24 hours. Aqueous sodium bicarbonate (100 ml., 10%) was added with stirring and cooling. After 1 hour the mixture was separated and the aqueous phase further extracted with chloroform. The chloroform solution, after washing with water was dried (MgSO$_4$), filtered, and evaporated to afford an oil, which, on addition of ether/petrol crystallised (1.149 g.). A sample (250 mg.) was recrystallised from ether/petrol to afford pure title compound (191 mg.) as white flakes; m.p. 147°-148°, $[\alpha]_D$ +94°, (c 0.55%).

Preparation 29

17β-Carbamoyl-5α-androstan-3-one

A solution of 5α-androstan-3-one 17β-carboxylic acid (2.25 g., corrected for the presence of 15% 5α-pregnan-3,20-dione as an impurity) and oxalyl chloride (4.5 ml.) in dry benzene (150 ml.) was refluxed for 1.5 hours, and then evaporated to dryness to afford crude 17β-chlorocarbonyl-5α-androstan-3-one. This acid chloride in benzene (15 ml.) was shaken with 880 ammonia (24 ml.) and water (15 ml.) for 5 minutes. After a further 30 minutes of standing at room temperature the precipitated amide was filtered, washed with water and dried. Recrysyallisation from dichloromethane/petrol afforded title compound (1.18 g.) m.p. 259°–262°. A further recrystallisation from dichloromethane/petrol provided an analytically pure sample; m.p. 276°–277°; $[\alpha]_D$ + 51.5°, (c 0.6%).

Preparation 30

17β-Cyano-5α-androstan-3-one

A solution of 17β-carbamoyl-5α-androstan-3-one (2.4 g.) and polyphosphate ester (12 g.) in chloroform (125 ml.) was refluxed for 24 hours. After removing the chloroform by evaporation aqueous 10% sodium carbonate (100 ml.) was added, the mixture cooled, and extracted with ether. The ethereal extracts were washed with water, dried (MgSO$_4$), filtered and evaporated to afford a buff solid (2.45 g.). Purification by preparative t.l.c. (ethanol/chloroform 1:19) afforded a solid (1.48 g.) which was further purified by passing through a florisil column and crystallisation from di-

39 chloromethane/petrol to give title compound (915 mg.) m.p. 150°-152°; [α]$_D$ + 89° (c 1.12%).

Preparation 31

17β-Carbamoyl-5α-androst-2-ene

A solution of 5α-androst-2-ene-17β-carboxylic acid (6.8 g.,) and oxalyl chloride (15 ml.) in dry benzene (150 ml.) was refluxed for 2 hours, before being evaporated to a residue. The residual acid chloride in benzene (50 ml.) was shaken vigorously with 880 ammonia (50 ml.) and water (20 ml.). After standing at room temperature for 4 hours the reaction mixture was filtered and the precipitate washed with water and dried. Recrystallisation from acetone/petrol afforded title compound (5.0 g.,) as white needles; m.p. 199°-202°; [α]$_D$ + 69°, (c 0.6).

Preparation 32  17β-Cyano-5α-androst-2-ene

A solution of 17β-carbamoyl-5α-androst-2-ene (4.33 g.,) and polyphosphate ester (25.0 g.) in chloroform (250 ml.) was refluxed for 16 hours. The residue, after removal of the chloroform, was neutralised by the careful addition of aqueous 10% sodium carbonate (150 ml.) with cooling and extracted with ether. The etheral solution was washed with water, dried (MgSO$_4$) filtered and evaporated to a partly crystalline residue which, after washing with a small portion of ice-cold ether, afforded a crystalline product (3.34 g.). The etheral washings were chromatographed on a column (1 inch × 6 inches) of florisil. Elution with petrol (200 ml.) afforded further product (660 mg.) gaining a total yield of 4.00 g. A sample (300 mg.) was recrystallised from petrol to afford title compound (260 mg.); m.p. 110°-112°: [α]$_D$ + 108°, (c 0.6).

Preparation 33

2β-Bromo-17β-cyano-3α-hydroxy-5α-androstane

A solution of 17β-cyano-5α-androst-2-ene, (3.70 g.,) and 85% m-chloroperbenzoic acid (3.0 g.) in chloroform (75 ml.) was stirred at room temperature for 1 hour and then washed successively with aqueous 10% sodium metabisulphite (20 ml.), aqueous 10% sodium bicarbonate (2 × 20 ml.) and water (20 ml.). To this solution of epoxide was added aqueous 48% hydrobromic acid (60 ml.) and the resulting biphasic mixture stirred vigorously at room temperature for 1.5 hours. A further portion of water (50 ml.) was added and the mixture separated. After washing with aqueous 10% sodium bicarbonate (2 × 25 ml.) and water (25 ml.), the chloroform solution was dried (MgSO$_4$), filtered and evaporated to afford a white froth (5.5 g.). Crystallisation from chloroform/petrol afforded title compound (3.42 g.,) in two crops; m.p. 162°-167°. A sample (300 mg.) was recrystallised from chloroform/petrol m.p. 167°-170°; [α]$_D$ + 54°, (c 0.8).

We claim:

1. A steroid of the androstane series having a 3α-hydroxy group, a 3β-hydrogen atom or methyl group, a 10-hydrogen atom or methyl group, two 11-hydrogen atoms or an 11-oxo group, a 17α-hydrogen atom, and a group at the 17β-position selected from the group consisting of

-COOR$^3$, -CN, -CHO and -CH(OR$^4$)$_2$ wherein R$^1$ is alkyl of 1–6 carbon atoms; phenyl; phenyl substituted by, alkoxy of 1–6 carbon atoms; benzyl or benzyl substituted by, alkoxy of 1–6 carbon atoms; R$^2$ is H or an R$^1$ group; or R$^1$ and R$^2$ together with the nitrogen atom to which they are attached represent a monocyclic heterocyclic ring having 5 or 6 ring members where R$^1$ and R$^2$ in said monocyclic heterocyclic ring are comprised of ring members selected from the group consisting of carbon atoms, carbon atoms and one nitrogen atom, carbon atoms and one oxygen atom and carbon atoms and one sulfur atom or such a ring substituted with alkyl of 1–6 carbon atoms; R$^3$ is alkyl of 1-10 carbon atoms; alkyl of 1–10 carbon atoms substituted with, hydroxy, lower alkanoyloxy of 1–6 carbon atoms, cyano, halo,

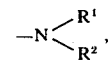

wherein R$^1$ and R$^2$ are as defined above except that R$^1$ may be H, ethoxycarbonyl, alkoxy of 1–10 carbon atoms, monocyclic nitrogen heterocyclic; phenyl; phenyl substituted with alkoxy of 1–6 carbon atoms or halogen, phenylalkyl having 1–6 carbon atoms in the alkyl moiety, monocyclic aralkyl having 1–6 carbon atoms in the alkyl moiety substituted in the monocyclic aryl portion with, alkoxy of 1–6 carbon atoms; R$^4$ is alkyl of 1–6 carbon atoms or (OR$^4$)$_2$ represents alkylene-dioxy of 2–6 carbon atoms; there being a hydrogen atom in the 5α-position and an oxo-group in the 11-position when there is a methoxycarbonyl, CHO or -CH(OR$^4$)$_2$ group in the 17β-position and the 3α-hydroxy steroid nucleus is saturated or has a double bond in the 1,2-position and is otherwise unsubstituted.

2. A steroid as claimed in claim 1 having a 5α-hydrogen atom.

3. A steriod as claimed in claim 1 having an 11-oxo-group and a 5α-hydrogen atom or 4,5-double bond.

4. A steroid as claimed in claim 1 having at the 17β-position a group of the formula -COOR$^3$ where R$^3$ is alkyl of 1–6 carbon atoms or alkyl of 1–6 carbon atoms substituted by hydroxy, lower alkanoyloxy of 1–6 carbon atoms or N-morpholino.

5. A steroid as claimed in claim 1 having at the 17β-position a group of the formula

wherein R$^1$ is alkyl of 1–4 carbon atoms and R$^2$ is alkyl of 1–4 carbon atoms or a hydrogen atom, or wherein R$^1$ and R$^2$ taken together with the nitrogen atom to which they are attached represent a heterocyclic ring which may contain an oxygen atom.

6. A steroid as claimed in claim 1 having at the 17β-position a group of the formula -COOR$^3$ where R$^3$ is (I) phenyl; (II) phenyl aryl substituted with lower alkoxy or halo of 1–6 carbon atoms; (III) benzyl wherein the alkyl moiety is of 1–6 carbon atoms; (IV) such benzyl group substituted with hydroxy, lower alkoxy or halo; (V) alkyl of 1–6 carbon atoms or (VI) alkyl or 1–6 carbon atoms substituted with acetoxyl, cyano, halo, alkyl, alkoxy of 1–6 carbon atoms or a group of the formula

wherein R¹ is H, alkyl of 1–6 carbon atoms, phenyl, phenyl substituted by hydroxy, alkoxy of 1–6 carbon atoms or halo, benzyl or benzyl substituted by hydroxy, alkoxy of 1–6 carbon atoms or halo and R² can be any of R¹ or R¹ and R² together with the nitrogen atom to which they are attached represent a heterocyclic ring which may contain an oxygen atom.

7. A steroid as claimed in claim 1 having at the 17β-position a group of the formula

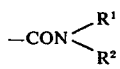

wherein R¹ is (i) alkyl of 1–6 carbon atoms, (ii) benzyl or (iii) phenyl; R² is H or an R¹ group or wherein R¹ and R² together with the nitrogen atom to which they are attached represent a heterocyclic ring which may contain an oxygen atom, or a group of the formula -CH(OR⁴)₂ where R⁴ is methyl or ethyl.

8. A steroid as claimed in claim 1 having at the 17β-position a cyano group.

9. A steroid as claimed in claim 1 wherein an alkyl or alkoxy group having 1–6 carbon atoms or a halogen atom is present at the 2β-position; a methyl group is present at the 16 -position; or wherein a 1,2- or 4,5-double bond is present.

10. A steroid as claimed in claim 1, which is:
3α-hydroxy-17β-methoxycarbonyl-5α-androstan-11-one;
3α-hydroxy-17β-ethoxycarbonyl-5α-androstan-11-one;
3α-hydroxy-17β-methoxycarbonylandrost-4-en-11-one;
3α-hydroxy-17β-dimethylcarbamoyl-5α-androstan-11-one;
3α-hydroxy-17β-(2'-morpholinoethoxycarbonyl)-5α-androstan-11-one, and the hydrochloride and citrate thereof;
3α-hydroxy-17β-cyano-5α-androstan-11-one;
3α-hydroxy-2β-methoxy-17β-metoxycarbonyl-5α-androstan-11-one;

11. A steroid as claimed in claim 1, which is: 3α-hydroxy-17β-methoxy-carbonyl-19-nor-5α-androstan-11-one;
3α-hydroxy-2β-ethoxy-17β-(2'-morpholinoethoxycarbonyl)-5α-androstan-11-one citrate;
17β-cyanomethoxycarbonyl-3α-hydroxy-5α-androstan-11-one;
3α-hydroxy-17β-(4'-morpholinobutoxycarbonyl)-5α-androstan-11-one;
17β-(3'-chloropropoxycarbonyl)-3α-hydroxy-5α-androstane-11-one;
3α-hydroxy-17β-(1-methyl-2'-morpholinoethoxycarbonyl)-5α-androstan-11-one;
3α-hydroxy-2β-ethoxy-17β-(2'-morpholinoethoxycarbonyl)-5α-androstan-11-one hydrochloride;
3α-hydroxy-17β-(2'-morpholinopropoxycarbonyl)-5α-androstan-11-one;
3α-hydroxy-2β-ethoxy-17β-(2'-morpholinoethoxycarbonyl)-5α-androstan-11-one mesylate, tartrate or dihydrogen phosphate;
3α-hydroxy-2β-ethoxy-17β-(2'-morpholinoethoxycarbonyl)-5α-androstan-11-one;
3α-hydroxy-17β-cyano-5α-androst-1-en-11-one;
3α-hydroxy-17β-(5-morpholinopentyloxy)-carbonyl-5α-androstan-11-one; and
3α-hydroxy-17β-(bismorpholinomethyl)-methoxycarbonyl-5α-androstan-11-one.

12. A steroid as claimed in claim 1 which possesses an acidic or basic group and is in the form of a salt with a base or an acid.

13. An intermediate for preparing a steriod as claimed in claim 1 comprising a steroid of the androstane series having a 3α-hydroxy group, a 3β-hydrogen atom or methyl group, a 10-hydrogen atom or methyl group, an 11-oxo group, a 5α-hydrogen atom or a 4,5-double bond and a 17β-carboxyl or carbamoyl group.

14. The compound of claim 1 which is 3α-hydroxy-17β-methoxycarbonyl-5α-androstan-11-one.

15. The compound of claim 1 which is 3α-hydroxy-17β-ethoxycarbonyl-5α-androstan-11-one.

16. The compound of claim 1 which is 3α-hydroxy-17β-methoxycarbonylandrost-4-en-11-one.

17. The compound of claim 1 which is 3α-hydroxy-17β-cyano-5α-androstan-11-one.

18. The compound of claim 1 which is 3α-hydroxy-2β-methoxy-17β-methoxycarbonyl-5α-androstan-11-one.

19. The compound of claim 1 which is 17β-cyanomethoxycarbonyl-3α-hydroxy-5α-androstan-11-one.

20. The compound of claim 1 which is 17β-(3'-chloropropoxycarbonyl)-3α-hydroxy-5α-androstan-11-one.

21. The compound of claim 1 which is 3α-hydroxy-2β-ethoxy-17β-(2'-morpholinoethoxycarbonyl)-5α-androstan-11-one mesylate.

22. The compound of claim 1 which is 3α-hydroxy-2β-ethoxy-17β-(2'-morpholinoethoxycarbonyl)-5α-androstan-11-one dihydrogen phosphate.

23. The compound of claim 1 which is 2β-bromo-17β-cyano-3α-hydroxy-5α-androstan-11-one.

24. The compound of claim 1 which is 17β-cyano-3α-hydroxy-5α-androst-1-en-11-one.

25. The compound of claim 1 which is 17β-Cyano-3α-hydroxy-5β-androstane.

26. The compound of claim 1 which is 17β-Cyano-3α-hydroxy-5β-androstan-11-one.

27. The compound of claim 1 which is 17β-Cyano-3α-hydroxy-5α-androstane.

28. The compound of claim 1 which is 17β-Cyano-3α-hydroxy-5α-androst-1-ene.

* * * * *